United States Patent
Onaga

(10) Patent No.: US 8,231,644 B2
(45) Date of Patent: Jul. 31, 2012

(54) TORQUE WRENCH AND ULTRASONIC SURGICAL DEVICE

(75) Inventor: Takeshi Onaga, Hachioji (JP)

(73) Assignee: Olympus Medical Systems Corp. (JP)

( * ) Notice: Subject to any disclaimer, the term of this patent is extended or adjusted under 35 U.S.C. 154(b) by 0 days.

(21) Appl. No.: 12/945,968

(22) Filed: Nov. 15, 2010

(65) Prior Publication Data

US 2011/0118631 A1  May 19, 2011

Related U.S. Application Data

(63) Continuation of application No. PCT/JP2010/061178, filed on Jun. 30, 2010.

(30) Foreign Application Priority Data

Aug. 5, 2009 (JP) ................................ 2009-182662

(51) Int. Cl.
*A61B 17/32* (2006.01)
(52) U.S. Cl. ................................. 606/169; 601/2; 81/60
(58) Field of Classification Search ..................... 606/27, 606/169; 81/60, 64, 467; 433/118, 141; 601/2
See application file for complete search history.

(56) References Cited

U.S. PATENT DOCUMENTS

| | | | | |
|---|---|---|---|---|
| 2,578,686 A | * | 12/1951 | Fish | ............................... 81/124.2 |
| 3,857,387 A | * | 12/1974 | Shock | ............................ 606/169 |
| 2008/0070190 A1 | | 3/2008 | Baumgartner | ................ 433/141 |

FOREIGN PATENT DOCUMENTS

| | | |
|---|---|---|
| JP | 2001-162549 | 6/2001 |
| JP | 3276631 | 4/2002 |
| JP | 2006-255803 | 9/2006 |
| JP | 2008-512254 | 4/2008 |
| JP | 2008-264994 | 11/2008 |

OTHER PUBLICATIONS

English translation of the International Search Report for corresponding International Application No. PCT/JP2010/061178 mailed on Aug. 3, 2010.
International Search Report and Written Opinion mailed Aug. 3, 2010 in corresponding PCT International Application No. PCT/JP2010/061178.

* cited by examiner

*Primary Examiner* — Victor Nguyen
(74) *Attorney, Agent, or Firm* — Ostrolenk Faber LLP

(57) ABSTRACT

A head portion includes an engaging portion capable of engaging with an engagement portion, a slit formed by cutting a part of a peripheral wall surface of the engaging portion, a protuberance which protrudes inward from the peripheral wall surface of the engaging portion, the protuberance including a slope the height of projection of which gradually increases along the circumference of the peripheral wall and which is oriented in a direction of rotation in a rotating operation, and a stop surface extending in radial directions of the engaging portion. The head portion includes an elastically deformable portion configured to cause at least one of two opposite side portions of the slit to be elastically deformed so that the slit is widened until a preset value is reached by the torque applied from the engaging portion to the engagement portion with the protuberance in mesh with an interlocking portion.

6 Claims, 17 Drawing Sheets

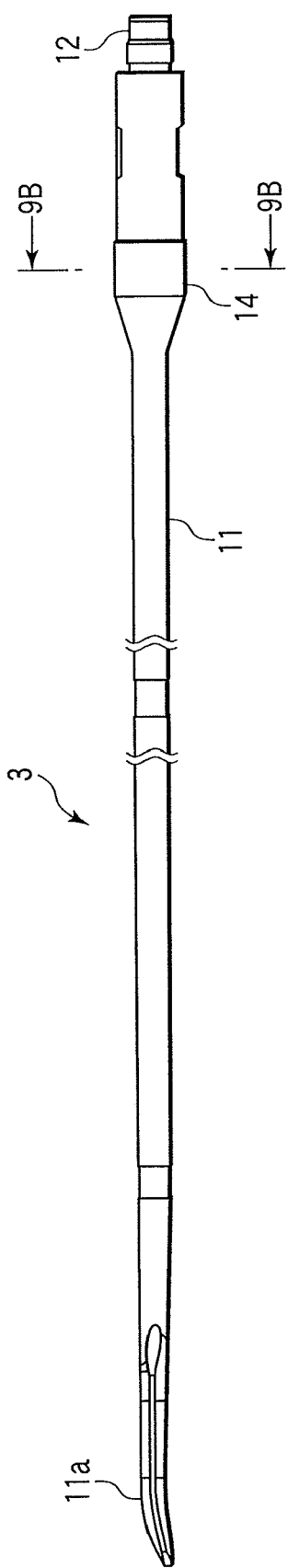
F I G. 9A

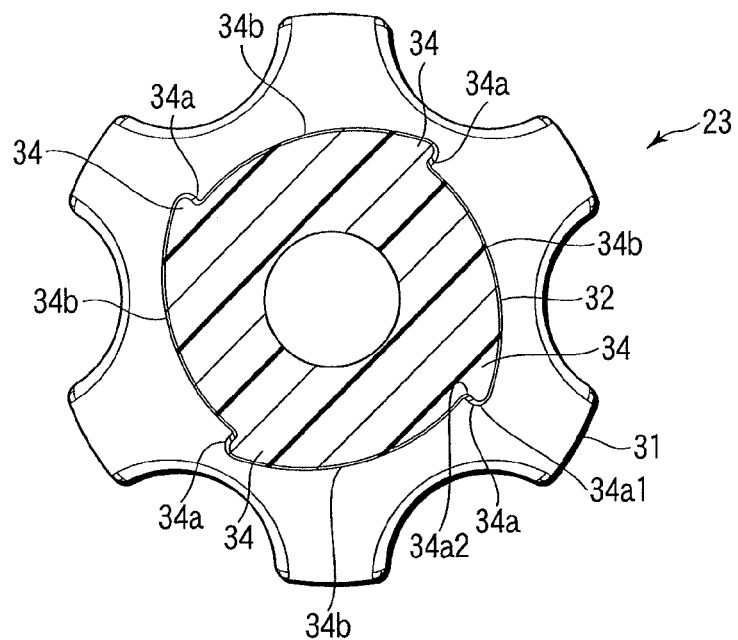
F I G. 13
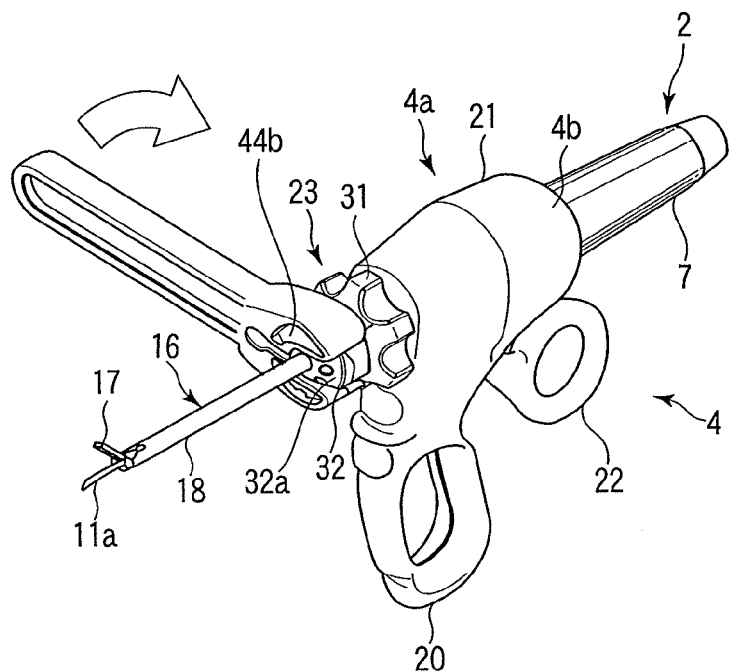
F I G. 14

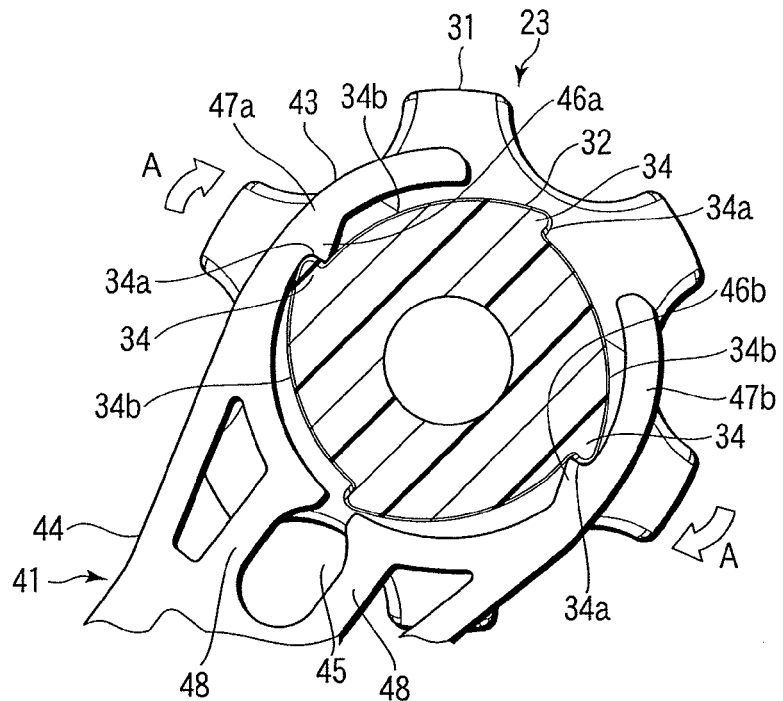
F I G. 15
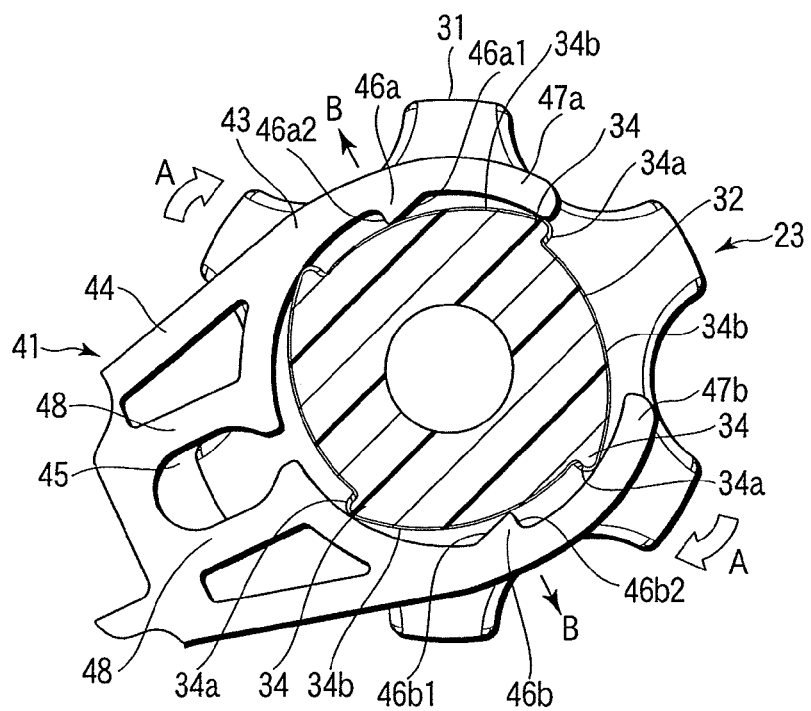
F I G. 16

TORQUE WRENCH AND ULTRASONIC SURGICAL DEVICE

CROSS REFERENCE TO RELATED APPLICATIONS

This is a Continuation Application of PCT Application No. PCT/JP2010/061178, filed Jun. 30, 2010, which was published under PCT Article 21(2) in Japanese.

This application is based upon and claims the benefit of priority from prior Japanese Patent Application No. 2009-182662, filed Aug. 5, 2009, the entire contents of which are incorporated herein by reference.

BACKGROUND OF THE INVENTION

1. Field of the Invention

The present invention relates to a torque wrench used for attachment and detachment of an ultrasonic vibrator and an ultrasonic probe, threadedly engaged with each other in an ultrasonic treatment instrument, and an ultrasonic surgical device.

2. Description of the Related Art

In general, an ultrasonic treatment device includes an ultrasonic vibrator, and an ultrasonic probe which transmits ultrasonic vibration output from the vibrator to a treatment section provided at the distal end of the treatment device. The ultrasonic vibrator and the probe are connected to each other by a threaded engagement portion. During use of the ultrasonic treatment device, the vibrator and the probe are attached to and detached from each other.

A tool that is used to attach/detach an ultrasonic vibrator and an ultrasonic probe to/from each other is disclosed in Japanese Patent No. 3276631. This tool includes a cylindrical member which applies torque to the probe of an ultrasonic treatment instrument, and an adapter used in combination with the cylindrical member. A ratchet-type torque adjustment mechanism that adjusts torque applied to the probe of the treatment instrument is provided between the cylindrical member and the adapter. The cylindrical member and the adapter are assembled together when the tool is operated to attach/detach the vibrator and probe to/from each other. In this state, the probe of the ultrasonic treatment instrument is passed through the cylindrical member, and the adapter is rotated around the axis of the probe so that the probe is screwed into the vibrator. As this is done, the torque applied to the probe of the treatment instrument is adjusted to a fixed value by the torque adjustment mechanism provided between the cylindrical member and the adapter.

A torque wrench that is used to attach/detach an ultrasonic vibrator and ultrasonic probe to/from each other is disclosed in Jpn. Pat. Appln. KOKAI Publication No. 2008-264994. This torque wrench includes an arm used as an operating section, a head portion, and an urging member such as a torsion coil spring. The head portion is pivotably mounted on the distal end of the arm and engages with an ultrasonic probe. The urging member is mounted on the arm and applies urging force to the head portion. A wrench receiving portion of the ultrasonic probe is introduced into an engaging recess of the head portion, and the head portion engages with the probe. The arm of the torque wrench is operated to apply torque to the probe with the head portion in engagement with the probe. By this tightening operation, the proximal end portion of the probe is screwed into and secured to the ultrasonic vibrator. If a preset value is exceeded by the torque thus applied to the wrench, the torsion coil spring contracts so that the head portion is pivoted around a pivot pin with respect to the arm as the operating section. Thus, the tightening torque on the ultrasonic probe can be adjusted to a fixed value during the tightening operation in which the proximal end portion of the probe is threadedly secured to the vibrator by the torque wrench.

A torque wrench described in Jpn. Pat. Appln. KOKAI Publication No. 2006-255803 is used to secure a probe of an ultrasonic surgical device to a vibrator with an appropriate torque. One part of this torque wrench is used to secure the probe to the vibrator, and another part of this torque wrench is used to remove them from each other.

BRIEF SUMMARY OF THE INVENTION

According to one aspect of the invention, a torque wrench used in attachment and detachment of an ultrasonic vibrator and an ultrasonic probe of an ultrasonic treatment instrument, includes: an arm portion which is held by a user; and a head portion which is provided on a distal end portion of the arm portion so as to be integral with the arm portion, and which is configured to releasably engage with an engagement portion disposed on the ultrasonic treatment instrument and to transmit torque to the engagement portion, wherein the head portion includes an engaging portion covering an outer peripheral surface of the engagement portion and capable of engaging with the engagement portion, a slit formed by cutting a part of a peripheral wall surface of the engaging portion, a protuberance which protrudes inward from the peripheral wall surface of the engaging portion, the protuberance including a slope the height of projection, from the peripheral wall surface, of which gradually increases along the circumference of the peripheral wall and which is oriented in a direction of rotation when the torque is transmitted to the engagement portion in a rotating operation such that the ultrasonic probe and the ultrasonic vibrator are threadedly engaged with each other, and a stop surface extending in radial directions of the engaging portion, and an elastically deformable portion configured to cause at least one of two opposite side portions of the slit to be elastically deformed so that the slit is widened until a preset value is reached by the torque applied from the engaging portion to the engagement portion with the protuberance in mesh with an interlocking portion formed on the outer peripheral surface of the engagement portion.

According to one other aspect of the invention, an ultrasonic surgical device includes: an ultrasonic treatment instrument including an ultrasonic vibrator configured to generate ultrasonic vibration, an ultrasonic probe threadedly engaged with the ultrasonic vibrator and capable of transmitting the ultrasonic vibration produced by the ultrasonic vibrator, and an engagement portion in which an interlocking portion is formed on an outer peripheral surface; and a torque wrench used in attachment and detachment of the ultrasonic vibrator and the ultrasonic probe, the torque wrench including an arm portion which is held by a user, and a head portion which is provided on a distal end portion of the arm portion so as to be integral with the arm portion and which is configured to releasably engage with the engagement portion of the ultrasonic treatment instrument and to transmit torque to the engagement portion, wherein the head portion includes an engaging portion covering an outer peripheral surface of the engagement portion and capable of engaging with the engagement portion, a slit formed by cutting a part of a peripheral wall surface of the engaging portion, a protuberance which protrudes inward from the peripheral wall surface of the engaging portion, the protuberance including a slope the height of projection, from the peripheral wall surface, of which gradually increases along the circumference of the peripheral wall and which is oriented in a direction of rotation when the torque is transmitted to the engagement portion in a rotating operation such that the ultrasonic probe and the ultrasonic vibrator are threadedly engaged with each other, and a stop surface extending in radial directions of the engaging portion, and an elastically deformable portion configured to cause at least one of two opposite side portions of the slit to be elastically deformed so that the slit is widened until a preset value is reached by the torque applied from the engaging portion to the engagement portion with the protuberance in mesh with the interlocking portion of the engagement portion.

Advantages of the invention will be set forth in the description which follows, and in part will be obvious from the description, or may be learned by practice of the invention. Advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 9A is a side view showing a probe of the ultrasonic treatment instrument available for the use of the torque wrench according to the first embodiment;

FIG. 13 is a cross-sectional view showing interlocking portions of the rotary knob of the ultrasonic treatment instrument available for the use of the torque wrench according to the first embodiment;

FIG. 14 is a view illustrating how the torque wrench according to the first embodiment is operated;

FIG. 15 is a plan view showing an initial state before the operative torque wrench according to the first embodiment is rotated in its tightening direction;

FIG. 16 is a plan view showing the operative torque wrench according to the first embodiment being rotated in the tightening direction;

DETAILED DESCRIPTION OF THE INVENTION

Figure 1:
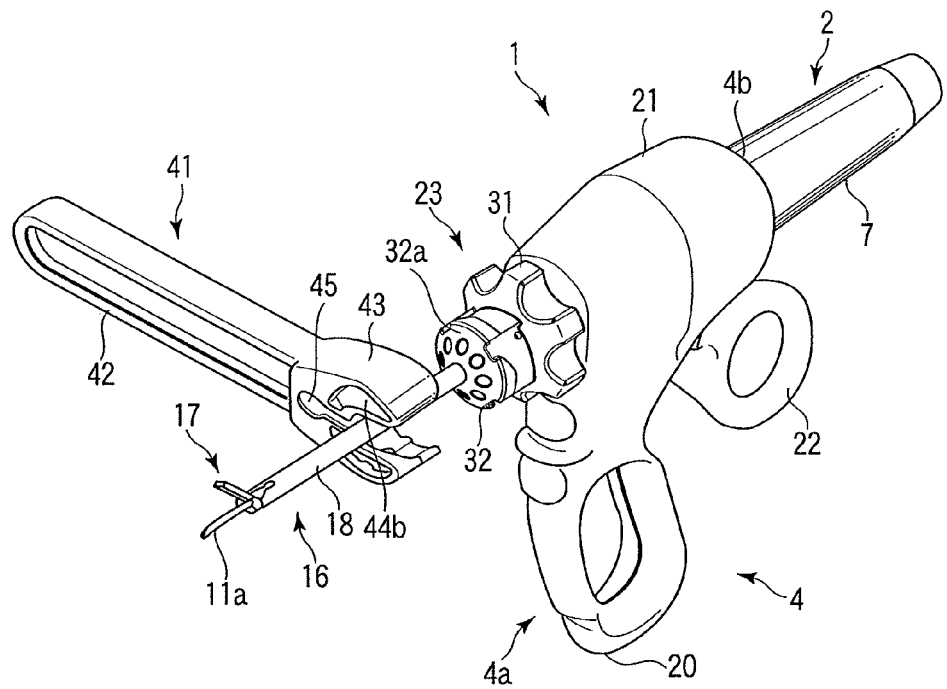
FIG. 1 is a perspective view showing how a torque wrench according to a first embodiment of the invention is operated to attach or detach a threaded engagement portion between an ultrasonic vibrator and an ultrasonic probe.

A first embodiment of the present invention will now be described with reference to FIGS. 1 to 18. FIG. 1 is a perspective view showing how a torque wrench 41 of the present embodiment is being secured to a hand piece 1 of an ultrasonic treatment instrument available for the use of the torque wrench 41. The ultrasonic treatment instrument of the present embodiment is an ultrasonic coagulating and cutting device capable of ultrasonically incising, excising, or coagulating living tissue and performing high-frequency treatment.

Figure 6:
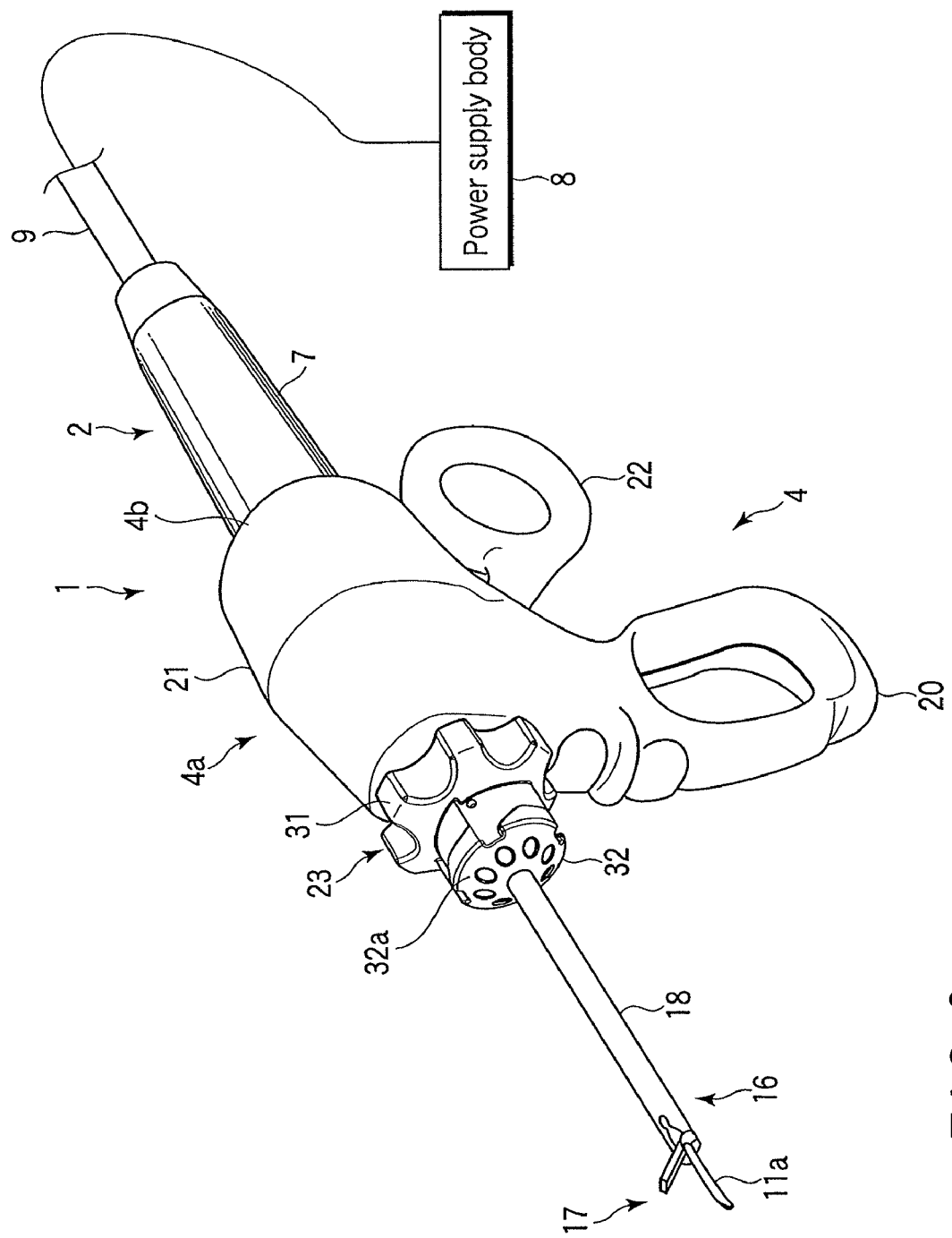
FIG. 6 is a perspective view showing an ultrasonic treatment instrument available for the use of the torque wrench according to the first embodiment.
Figure 7:
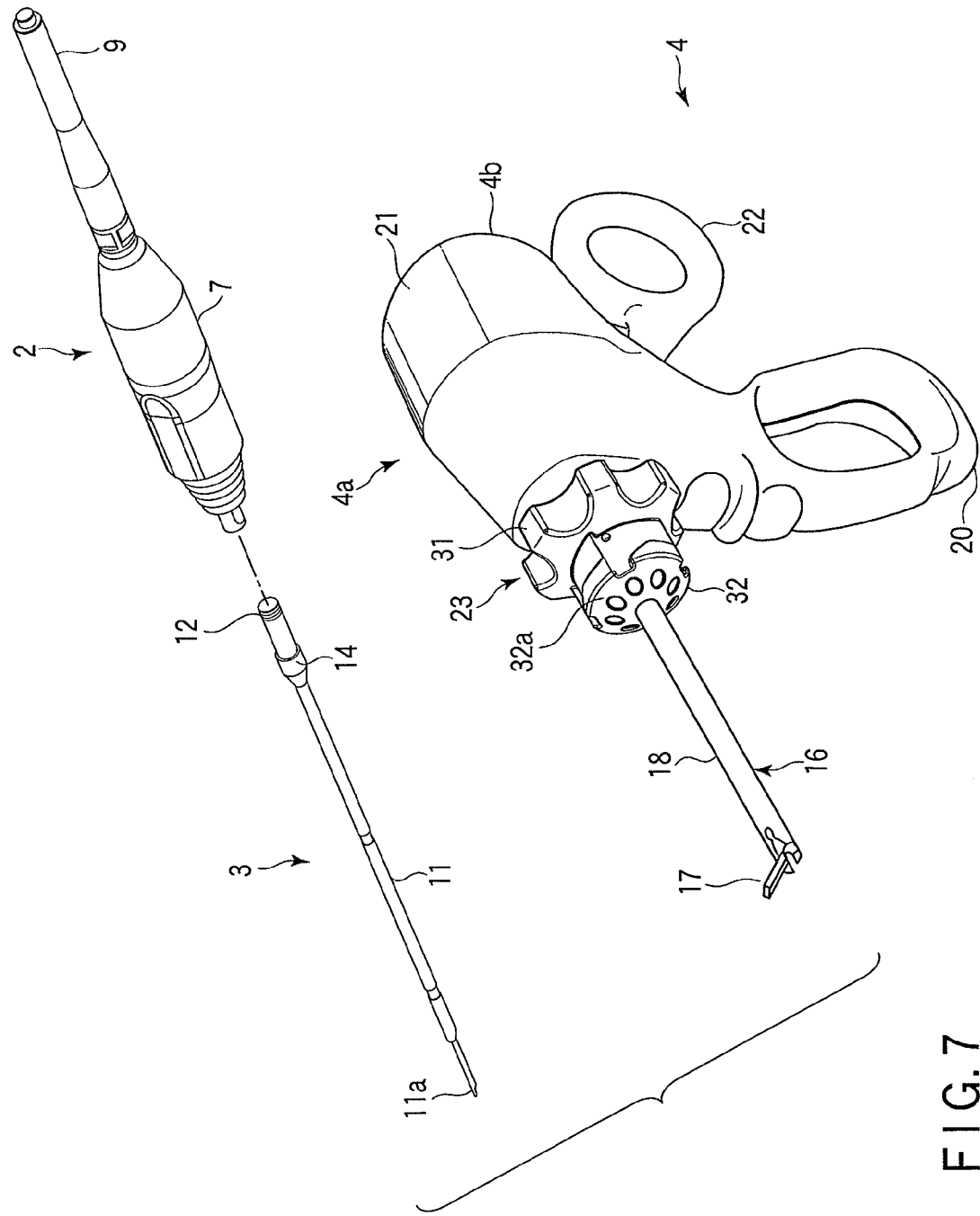
FIG. 7 is an exploded perspective view showing the ultrasonic treatment instrument available for the use of the torque wrench according to the first embodiment.

FIGS. 6 and 7 are views showing the hand piece 1 of the ultrasonic treatment instrument. As shown in FIGS. 6 and 7, the hand piece 1 includes three units, which are a vibrator unit 2, a probe unit (probe section) 3, and a handle unit (handle section) 4. These three units 2 to 4 are removably connected to one another.

A vibrator 6 (FIG. 10) is incorporated in the vibrator unit 2. The vibrator 6 generates ultrasonic vibration by a piezoelectric element which converts current into ultrasonic vibration.

Figure 10:
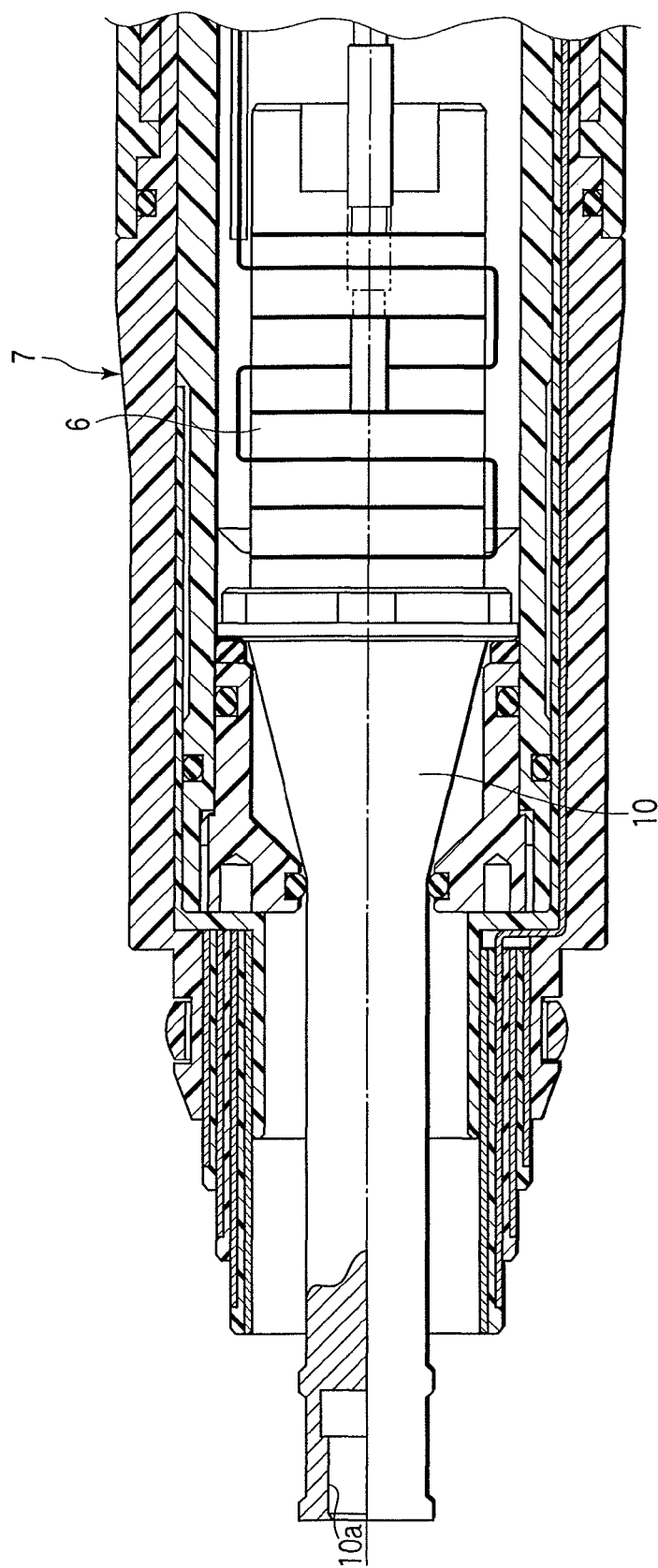
FIG. 10 is a longitudinal sectional view showing a threaded hole part of the ultrasonic vibrator of the ultrasonic treatment instrument available for the use of the torque wrench according to the first embodiment.

The vibrator 6 is externally covered by a cylindrical vibrator cover 7. Further, a cable 9 through which the current generating the ultrasonic vibration is supplied from a power supply body 8 extends to the rear end of the vibrator unit 2. As shown in FIG. 10, the proximal end portion of a horn 10 that serves to increase the amplitude of the ultrasonic vibration is connected to the front end portion of the ultrasonic vibrator 6 within the vibrator cover 7. A threaded hole portion 10a used in probe mounting is formed in the distal end portion of the horn 10.

FIG. 9A is a view showing an appearance of the entire of the probe unit 3. The probe unit 3 includes an ultrasonic probe 11 which is a metallic rod-like vibration transmission member. A screw portion 12 that threadedly engages with the threaded hole portion 10a of the horn 10 is disposed at the proximal end of the ultrasonic probe 11. The screw portion 12 of the ultrasonic probe 11 is screwed into the threaded hole portion 10a of the horn 10 of the vibrator unit 2 by the torque wrench 41 of the present embodiment which will be described later. Thus, the ultrasonic probe 11 and vibrator 6 are assembled to each other.

Figure 9B:
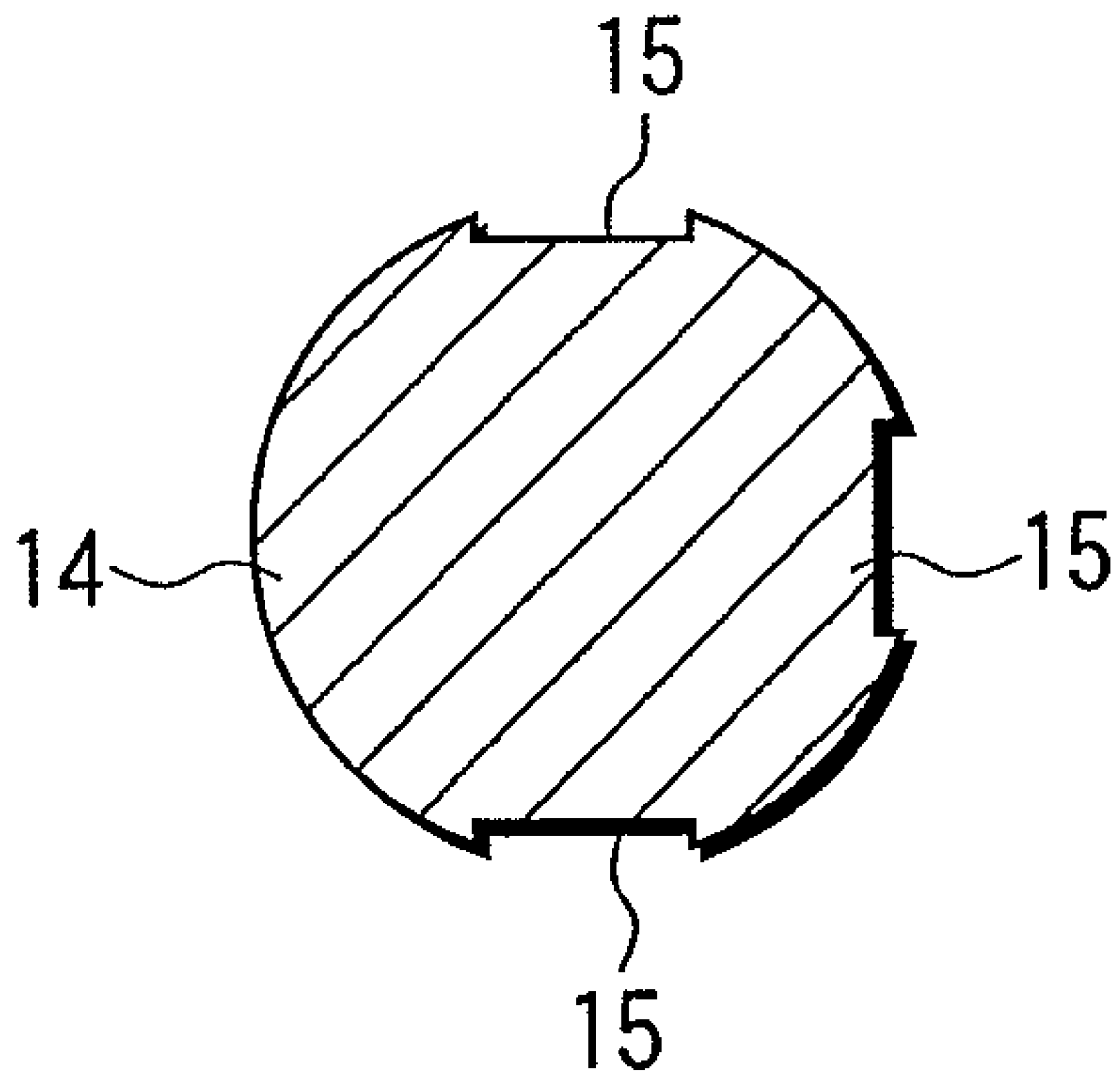
FIG. 9B is a sectional view taken along line 9B-9B of FIG. 9A.

As shown in FIG. 9A, a probe distal end 11a is disposed at the distal end of the ultrasonic probe 11. The probe distal end 11a is substantially J-shaped. A flange portion 14 is disposed in a position corresponding to a vibration node on the most proximal end side in axial directions of the probe unit 3. As shown in FIG. 9B, three engaging recesses 15 in the form of key grooves are formed at circumferential intervals in the outer peripheral surface of the flange portion 14.

As shown in FIG. 7, the handle unit 4 includes an elongated sheath body 16, a jaw 17 provided at the distal end of the sheath body 16, and an operation section 4a provided at the proximal end of the sheath body 16. The sheath body 16 is an insertion section to be inserted into a patient's body. The operation section 4a of the handle unit 4 includes a substantially cylindrical holding barrel 21. A vibrator junction 4b is formed at the proximal end of the holding barrel 21.

The sheath body 16 includes a metallic outer sheath 18, and a metallic drive pipe (drive member) used as an inner sheath (not shown). The drive pipe is axially movable in the outer sheath 18. The proximal end of the outer sheath 18, together with a rotary knob 23 (described later), is mounted on the distal end of the holding barrel 21. The outer sheath 18 is rotatable around its central axis.

Figure 8:
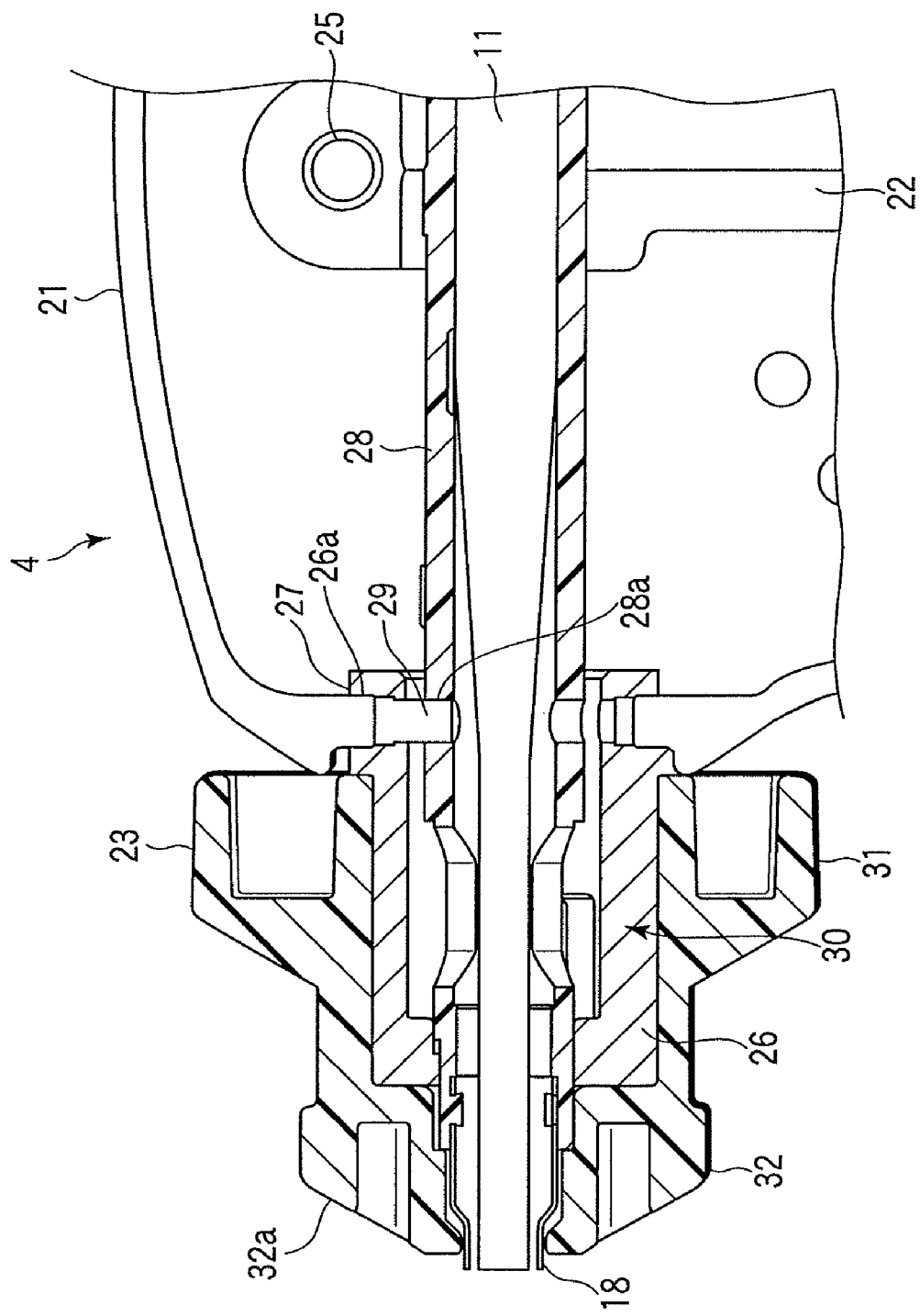
FIG. 8 is a longitudinal sectional view showing the internal structure of a handle of the ultrasonic treatment instrument available for the use of the torque wrench according to the first embodiment.

Further, the holding barrel 21 includes a fixed handle 20, and movable handle 22 pivotable relative to the fixed handle. An acting pin (not shown) and a support pin 25 (FIG. 8) are arranged on the upper end portion of the movable handle 22. As shown in FIG. 8, the upper end portion of the movable handle 22 is pivotably connected to the holding barrel 21 by the support pin 25.

The holding barrel 21 contains therein an operating force transmission mechanism (not shown) which transmits the operating force of the movable handle 22 to the drive pipe of the jaw 17. The acting pin of the movable handle 22 is connected to the operating force transmission mechanism.

When the movable handle 22 is closed with respect to the fixed handle 20, the acting pin pivots around the support pin 25 as the movable handle 22 pivots. As the acting pin acts in this manner, the operating force is transmitted to the drive pipe by the operating force transmission mechanism, and then the drive pipe is driven axially. As the drive pipe thus axially advances or retreats, the driving force of the drive pipe is transmitted to the jaw 17. If the drive pipe is pulled back, the jaw 17 is driven away from the probe distal end 11a (to take an open position). If the drive pipe is pushed out forward, in contrast, the jaw 17 is driven toward the probe distal end 11a (to take a closed position). As the jaw 17 is pivoted to the closed position, living tissue is held between the jaw 17 and the probe distal end 11a of the probe unit 3.

The rotary knob 23 is connected to the front end portion of the holding barrel 21 so as to be rotatable around the axis of the ultrasonic probe 11. FIG. 8 shows a mounting structure of the rotary knob 23. A cylindrical knob receiving member 26 is disposed on the inner peripheral surface of the rotary knob 23. The inner peripheral surface of the knob 23 and the outer peripheral surface of the receiving member 26 are secured to each other by an anti-rotation portion (not shown) that includes a key and key groove. The anti-rotation portion prevents the knob 23 and the receiving member 26 from rotating relative to each other.

The proximal end of the knob receiving member 26 is connected to the front end of the holding barrel 21 through a bearing 27 so as to be rotatable around the axis of the ultrasonic probe 11. A tubular probe holder 28 that covers the ultrasonic probe 11 is located inside the knob receiving member 26. A pin insertion hole 26a is radially extend through the knob receiving member 26, and a pin insertion hole 28a is radially extend through the probe holder 28, respectively. A connecting pin 29 is passed through the insertion hole 26a of the receiving member 26 and the insertion hole 28a of the probe holder 28. The receiving member 26 and the probe holder 28 are secured to each other by the connecting pin 29 so that they cannot rotate relative to each other.

The inner peripheral surface of the probe holder 28 and the outer peripheral surface of the ultrasonic probe 11 are secured to each other by an anti-rotation portion (not shown) that includes a key and key groove. In this way, the probe holder 28 and probe 11 are prevented from rotating relative to each other.

The proximal end of the outer sheath 18 is connected to the distal end of the probe holder 28. If the rotary knob 23 is rotated, the knob receiving member 26 rotates together with the knob 23. As this is done, the rotation of the receiving member 26 is transmitted to the probe holder 28 through the connecting pin 29. Further, the rotation of the probe holder 28 is transmitted to the ultrasonic probe 11 through the anti-rotation portion (not shown) including the key and key groove. Thus, the rotation of the knob 23 is transmitted to the ultrasonic probe 11 through the receiving member 26, the pin 29, and the holder 28 in the order named, and then the probe 11 rotates together with the knob 23. Specifically, the knob 23, the receiving member 26, the pin 29, and the holder 28 constitute a torque transmission portion 30, which transmits torque to the probe 11 produced around the axis of the probe 11 by the knob 23.

If the rotary knob 23 is rotated, furthermore, the outer sheath 18 is rotated together with the knob 23 around its central axis with respect to the holding barrel 21. Thus, when the knob 23 is rotated, the ultrasonic probe 11 and the outer sheath 18 of the sheath body 16 are simultaneously rotated around the central axis of the outer sheath 18. Consequently, the jaw 17 and the distal end 11a of the probe 11 are simultaneously rotated in the same direction.

Figure 11:
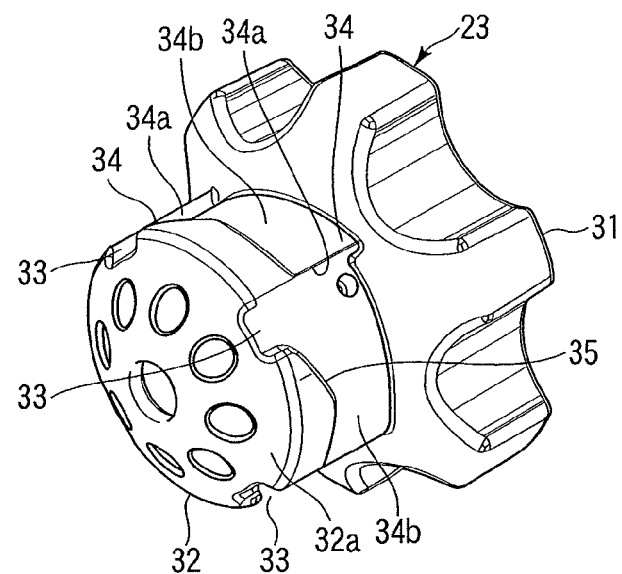
FIG. 11 is a perspective view showing an appearance of a rotary knob of the ultrasonic treatment instrument available for the use of the torque wrench according to the first embodiment.
Figure 12:
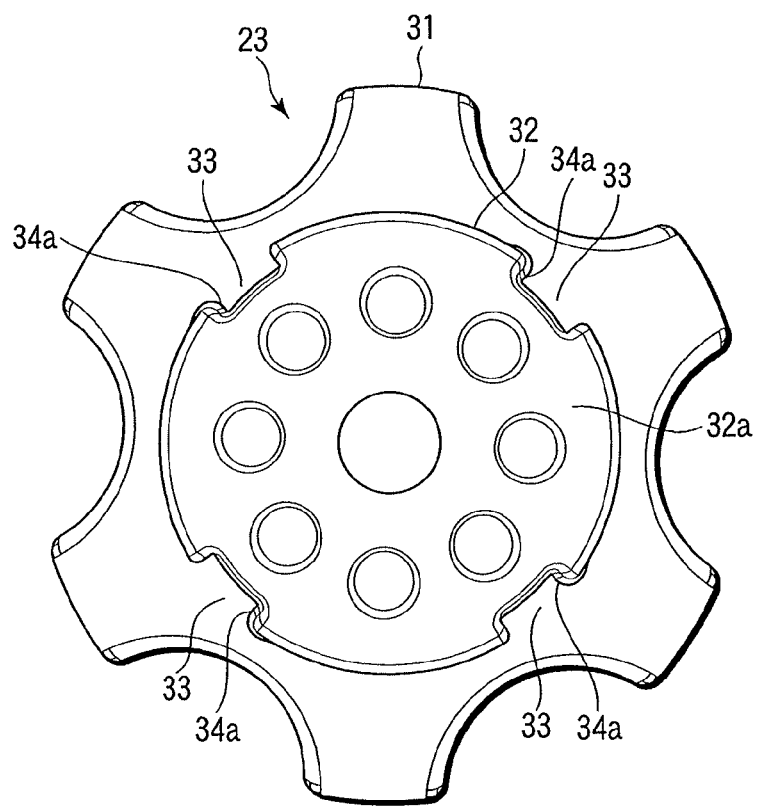
FIG. 12 is a plan view of the rotary knob of the ultrasonic treatment instrument available for the use of the torque wrench according to the first embodiment.

FIGS. 11 to 13 show the rotary knob 23. As shown in FIG. 11, the knob 23 includes a cylindrical boss portion (engagement portion) 32 that serves as a torque wrench receiving portion provided on the distal end of a knob body 31. As shown in FIG. 12, recesses 33 (four recesses in the case of the present embodiment) are circumferentially arranged at regular intervals on the outer peripheral surface of the front end portion of the boss portion 32. Each of the recesses 33 extends along the axis of the ultrasonic probe 11. An abutting surface 32a is formed on the front end of the boss portion 32. When the probe 11 is tightened, the abutting surface 32a abuts an abutting surface of a head of the torque wrench.

As shown in FIG. 13, four interlocking portions 34 are formed on the outer peripheral surface of the boss portion 32. Each interlocking portion 34 includes a straight vertical wall portion 34a, and substantially arcuate slope 34b. The slope 34b extends between a top position 34a1 of the vertical wall portion 34a and a bottom position 34a2 of its adjacent vertical wall portion 34a.

The vertical wall portion 34a of each interlocking portion 34 is formed in radial directions of the knob body 31. Each vertical wall portion 34a defines one side portion of its corresponding recess 33. As shown in FIG. 11, a guide portion 35 cut in the form of a slope is formed on the other side portion of each recess 33. Each guide portion 35 moves protuberances 46a and 46b (described later) of the torque wrench 41 toward the longitudinally proximal end of the insertion section of the hand piece 1 and guides them to the interlocking portions 34. Although the protuberances are moved toward the longitudinally proximal end in the present embodiment, they may alternatively be moved toward longitudinally the distal end. In the case of a bent insertion section including a bent portion, moreover, the protuberances may be configured to be moved in one direction along the axis of the bent portion.

Figure 2:
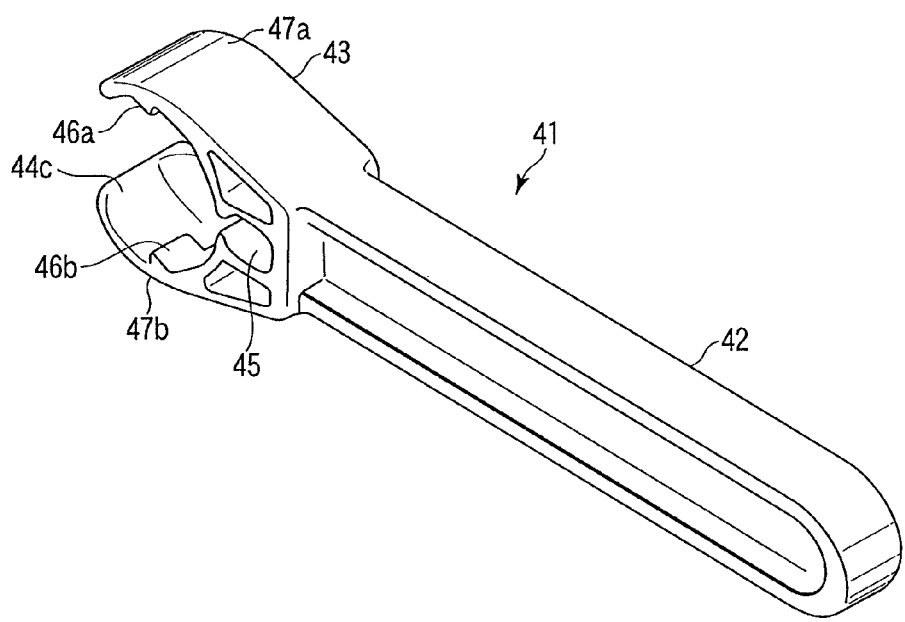
FIG. 2 is a perspective view showing an appearance of the torque wrench according to the first embodiment.

FIG. 2 is a view showing an appearance of the torque wrench 41 of the present embodiment available for attachment and detachment between the screw portion 12 of the ultrasonic probe 11 and the threaded hole portion 10a of the horn 10 of the vibrator unit 2. The torque wrench 41 includes a straight arm 42 used as an operating section, and a head 43 used of torque transmission. The head 43 is integrally provided on the distal end portion of the arm 42. In the torque wrench 41, the arm 42 and the head 43 are integrally molded of, for example, a resin material. Alternatively, the arm 42 and the head 43 may be integrally molded of a metallic material.

The head 43 includes a head body 44 capable of engaging with and entirely covering the boss portion 32 of rotary knob 23 of the ultrasonic treatment instrument. An engaging portion 44c that covers the entire boss portion 32 of the knob 23 is formed inside the head body 44.

Figure 3:
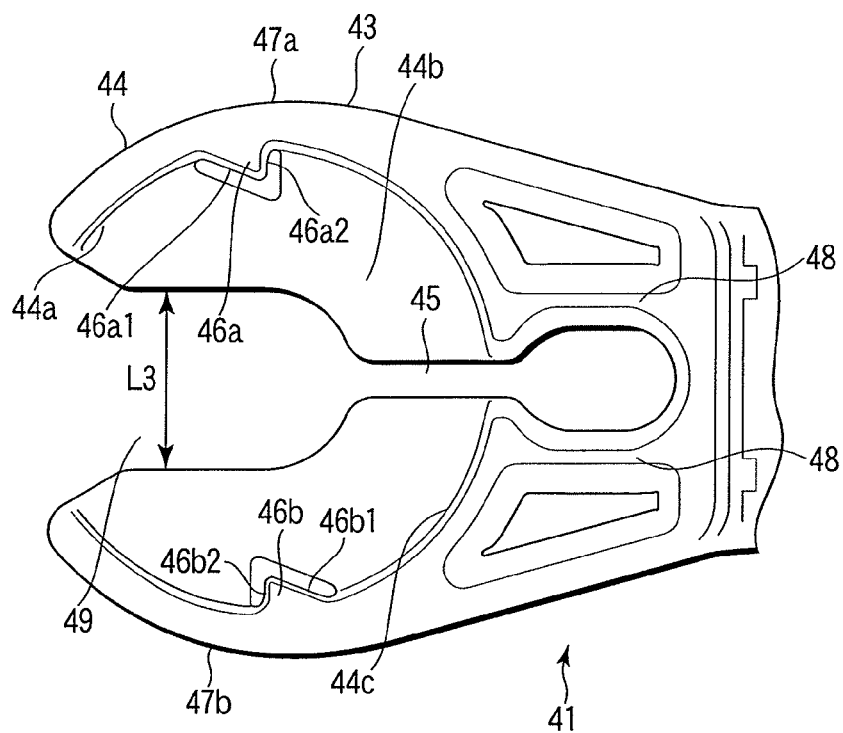
FIG. 3 is a plan view showing a head portion of the torque wrench according to the first embodiment.
Figure 4:
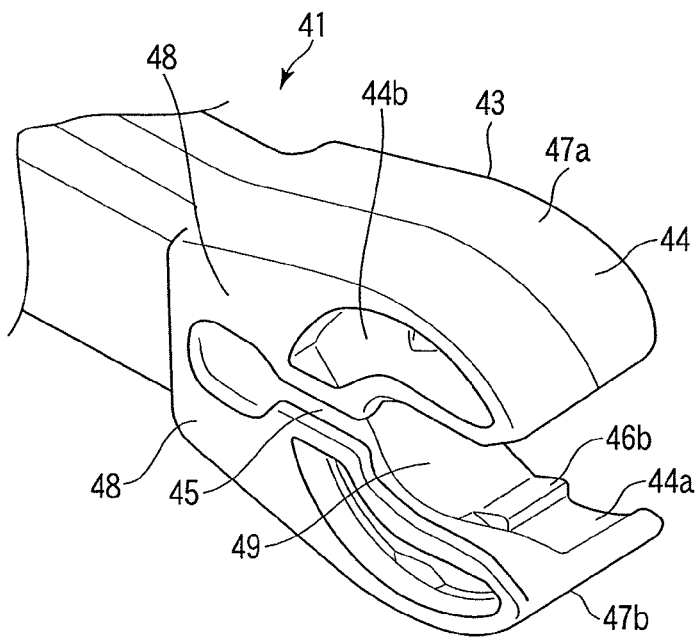
FIG. 4 is a perspective view showing the back of the head portion of the torque wrench according to the first embodiment.

As shown in FIG. 3, the head body 44 includes a slit 45, the two protuberances 46a and 46b, and an abutting surface 44b. The slit 45 extends along the center line of the arm 42. The protuberances 46a and 46b protrude inward from the inner peripheral surface of the head body 44. The abutting surface 44b is configured to be abutted against the boss portion 32 of the ultrasonic treatment instrument. The slit 45 is formed by cutting a part of a peripheral wall surface 44a of the head body 44. Thus, the head body 44 is substantially C-shaped as a whole. Although the two protuberances 46a and 46b are formed protruding from the inner peripheral surface of the head body 44 in the present embodiment, only one of them may be provided with the same effect. The abutting surface 44b of the head body 44 is shaped corresponding to the abutting surface 32a of the boss portion 32. Thus, the shape of the abutting surface 44b of the torque wrench 41 corresponds to that of the abutting surface 32a of the boss portion 32 of the ultrasonic treatment instrument. When the torque wrench 41 is secured to the boss portion 32 of the ultrasonic treatment instrument, therefore, its axial and circumferential backlashes can be suppressed. Therefore a dispersion of the tightening torque can be suppressed.

When the torque wrench 41 is set on the boss portion 32 provided at the proximal end of the sheath body 16 of the ultrasonic treatment instrument, moreover, the protuberances 46a and 46b of the head body 44 of the torque wrench 41 are guided by the sloped guide portion 35 of the rotary knob 23.

The protuberances 46a and 46b of the head body 44 are guided so that they move along the guide portion 35 toward the longitudinally proximal end of the sheath body 16 (on the opposite side to the direction of disengagement of the head 43). As the torque wrench 41 tightens the probe 11, therefore, it automatically moves toward the axially proximal end of the sheath body 16. Accordingly, the wrench 41 cannot be disengaged on the axially distal end side of the sheath body 16 while tightening the probe, so that a user can easily operate it. Thus, the protuberances 46a and 46b of the head body 44 of the wrench 41 can be easily set on the boss portion 32 of the sheath body 16 of the ultrasonic treatment instrument.

Figure 5:
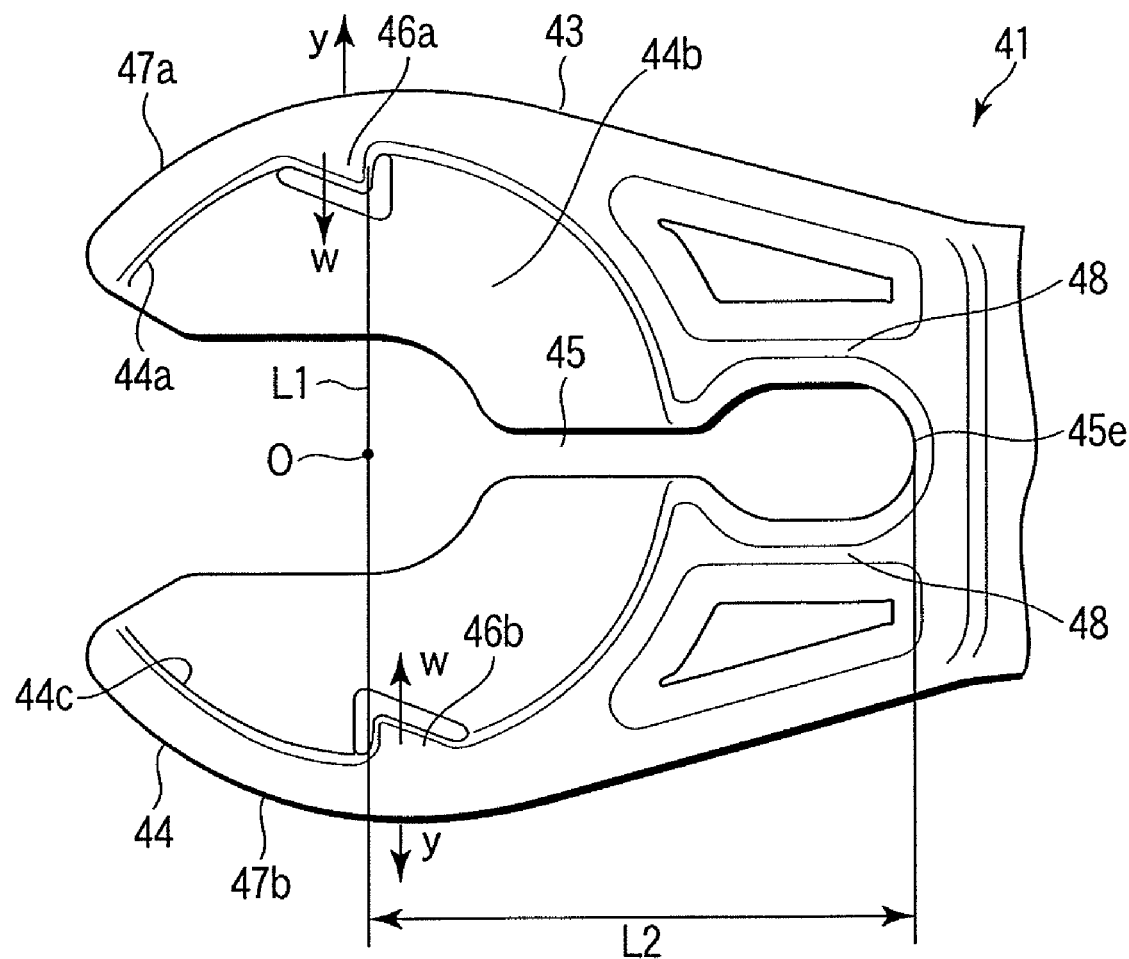
FIG. 5 is a view explaining a computational formula calculating an amount of force with which the probe is secured to the ultrasonic vibrator by the torque wrench according to the first embodiment.

As shown in FIG. 5, the slit 45 extends from the distal end position of the head body 44 toward the arm 42 through center position O of the peripheral wall surface 44a of the head body 44. Thus, two engaging arms 47a and 47b are formed individually on the opposite side of the slit 45 of the head body 44. The one protuberance 46a is located on the inner peripheral surface of the one engaging arm 47a, and the other protuberance 46b is located on the inner peripheral surface of the other engaging arm 47b.

Line L1 that connects the respective tops of the two protuberances 46a and 46b passes center position O of the peripheral wall surface 44a of the head body 44. Further, an end position (bottom) 45e of the slit 45 is located so that its horizontal distance L2 from the top of each of the protuberances 46a and 46b has a preset value.

As shown in FIG. 3, the protuberance 46a includes a slope 46a1 and a stop surface 46a2, while the protuberance 46b includes a slope 46b1 and a stop surface 46b2. The height of projection of each of the slopes 46a1 and 46b1 from the peripheral wall surface 44a of the head body 44 gradually increases along the circumference of the head body 44. Each of the stop surfaces 46a2 and 46b2 is formed of a vertical surface that extends in the radial directions of the head body 44. When the torque wrench 41 is actually used, as shown in FIG. 14, the two engaging arms 47a and 47b (the engaging portion 44c) of the head 43 are caused to releasably engage with the boss portion 32 of the rotary knob 23 so as to cover the entire knob 23. When this is done, the protuberance 46a is guided from one of the recesses 33 provided in the outer peripheral surface of the boss portion 32 to the interlocking portion 34 corresponding to the recess 33 through the corresponding guide portion 35. Likewise, the protuberance 46b is guided from another recess 33 to its corresponding interlocking portion 34.

Figure 17:
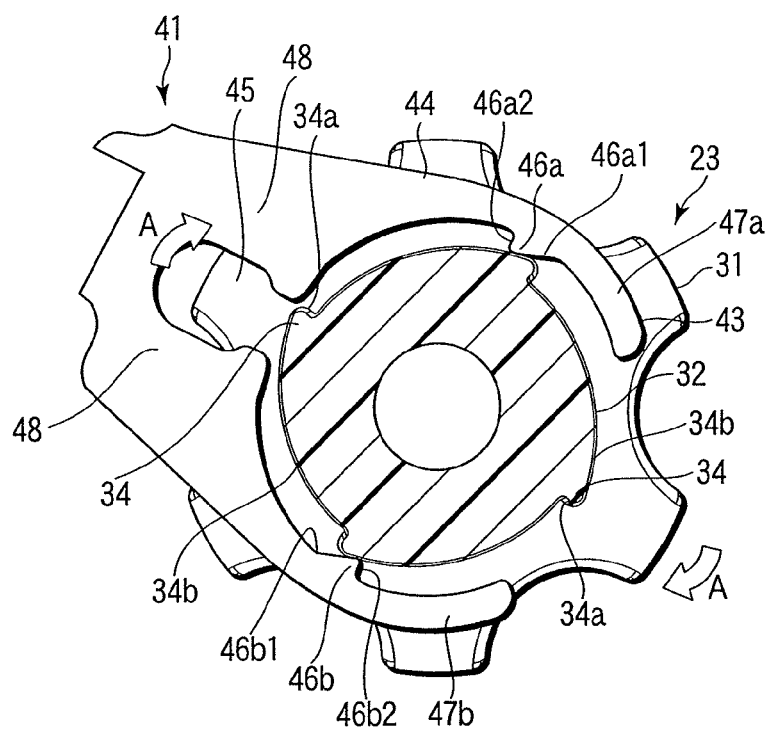
FIG. 17 is a plan view showing a state just before the operative torque wrench according to the first embodiment is rotated to its final rotational position of the tightening direction.
Figure 18:
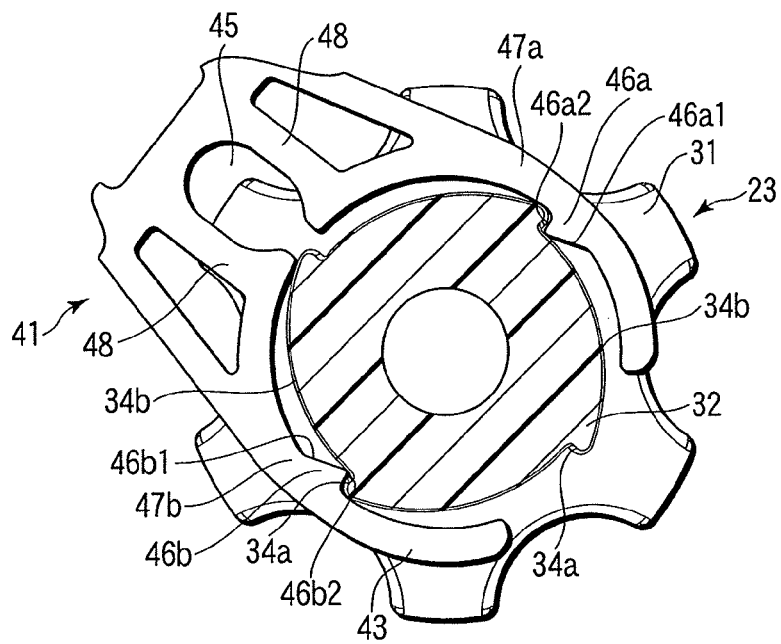
FIG. 18 is a plan view showing a state in which the operative torque wrench according to the first embodiment is in the final rotational position of the tightening direction.

In screwing the ultrasonic probe 11 into the threaded hole portion 10a of the horn 10 of the ultrasonic vibrator 6, the screw portion 12 of the probe 11 is located so that the slopes 46a1 and 46b1 are oriented in the direction of rotation (indicated by arrows A in FIG. 15) by which the screw portion 12 is tightened into the threaded hole portion 10a. Then, the torque wrench 41 is rotated clockwise, as indicated by arrows A in FIG. 15, with the two engaging arms 47a and 47b in engagement with the boss portion 32 and with one of the interlocking portion 34 on the outer peripheral surface of the boss portion 32 in mesh with the protuberance 46a and another interlocking portion 34 in mesh with the protuberance 46b, individually. Thus, torque is applied from the arms 47a and 47b to the boss portion 32. As this is done, as indicated by arrows B in FIG. 16, those parts of the arms 47a and 47b which are located individually on the opposite sides of the slit 45 are elastically deformed in such a direction that the slit 45 is spread. FIG. 17 shows how the arms are elastically deformed so that the slit 45 is maximally spread. When a predetermined level (state of FIG. 17) is exceeded by the torque applied to the boss portion 32, the engaging arms 47a and 47b are elastically deformed so that the protuberances 46a and 46b are disengaged from their corresponding interlocking portions 34, as shown in FIG. 18. In this way, elastically deformable portions 48 of the head body 44 are formed that prevent torque greater than a predetermined value from being applied to the boss portion 32.

FIG. 5 is a view explaining a computational formula used in calculating an appropriate amount of force with which the screw portion 12 of the ultrasonic probe 11 is tightened into the threaded hole portion 10a of the horn 10 of the ultrasonic vibrator 6 by the torque wrench 41 of the present embodiment. The required amount of force to tighten the screw portion 12 into the threaded hole portion 10a is set depending on reactive force W that is produced in the two engaging arms 47a and 47b when the slit 45 of the head 43 of the wrench 41 is opened. This reactive force W is given as follows:

$$W=(3 \times E \times I \times y)/(L2)^3,$$

where E is a Young's modulus, I is a second moment of area, y is a displacement of each of the protuberances 46a and 46b, and L2 is a horizontal distance from the end position 45e of the slit 45 to each protuberance. If these parameters are set to appropriate values, an appropriate reactive force (W) can be produced when the torque is applied to the boss portion 32 by the torque wrench 41. Thus, reactive force that satisfies an appropriate amount of tightening force can be set.

In the head body 44 of the torque wrench 41, moreover, a wide portion 49 is formed on the distal end side of the slit 45. Slit width L3 of the wide portion 49 is greater than the outside diameter of the outer sheath 18 of the sheath body 16 of the hand piece 1 of the ultrasonic treatment instrument. In securing the wrench 41 to the hand piece 1 of the treatment instrument, therefore, the outer sheath 18 of the hand piece 1 can be passed through the wide portion 49 of the slit 45 of the head body 44.

The following is a description of the operation of the structure described above. The torque wrench 41 of the present embodiment is used to tighten the screw portion 12 of the ultrasonic probe 11 into the threaded hole portion 10a of the horn 10 of the ultrasonic vibrator 6 in assembling the hand piece 1 of the ultrasonic treatment instrument. In operation, the torque wrench 41 is secured to the hand piece 1 of the ultrasonic treatment instrument. In doing this, the outer sheath 18 of the hand piece 1 is passed through the wide portion 49 of the slit 45 of the torque wrench 41, as shown in FIG. 1. In this state, the head 43 of the torque wrench 41 is slid to the proximal end portion of the outer sheath 18 and caused to releasably engage with the boss portion 32 of the ultrasonic treatment instrument, as shown in FIG. 14. When this is done, the protuberance 46a of the head body 44 is introduced from one of the recesses 33 provided in the outer peripheral surface of the boss portion 32 into a region on the outer peripheral surface side of the boss portion. Likewise, the protuberance 46b is introduced from another recess 33 into a region on the outer peripheral surface side of the boss portion 32. Further, the protuberances 46a and 46b are guided individually through their corresponding guide portions 35 to the interlocking portions 34 corresponding to the recesses 33 into which each of them is introduced. Thus, the head 43 of the torque wrench 41 is set in such a state that it is in releasable engagement with the boss portion 32 of the treatment instrument. In the set state, as shown in FIG. 15, the two engaging arms 47a and 47b engage with the boss portion 32, and one of the interlocking portions 34 formed on the outer peripheral surface of the boss portion 32 is kept in mesh with the protuberance 46a, and another interlocking portion 34 is kept mesh with the protuberance 46b. As this is done, the torque wrench 41 is held in its initial state before it is rotated in its tightening direction.

Thereafter, the torque wrench 41 is rotated clockwise, as indicated by arrow A in FIG. 15. By this operation, torques are individually transmitted from the protuberances 46a and 46b of the wrench 41 to the interlocking portions 34 of the boss portion 32. When this is done, tightening force that acts on the boss portion 32 of the rotary knob 23 is transmitted from the knob 23 to the ultrasonic probe 11 through the knob receiving member 26, the connecting pin 29, and the probe holder 28 in the order named. Thereupon, the probe 11 rotates together with the knob 23, and tightening torque, that causes the screw portion 12 of the probe 11 to rotate so as to be tightened into the threaded hole portion 10a of the horn 10 of the ultrasonic vibrator 6, is transmitted.

When the torque wrench 41 is rotated clockwise, moreover, each of its protuberances 46a and 46b moves from the bottom position 34a2 of the vertical wall portion 34a of its corresponding interlocking portion 34 of the boss portion 32 toward the top position 34a1 of the adjacent vertical wall portion 34a in such a manner that it slides on the slope 34b of the interlocking portion 34, as shown in FIG. 16. Thus, as the protuberances 46a and 46b slide individually on the respective slopes 34b of their corresponding interlocking portions 34, the slit 45 between the two engaging arms 47a and 47b of the head body 44 is gradually widened, so that the head body 44 is elastically deformed.

When each of the protuberances 46a and 46b of the torque wrench 41, sliding on the slope 34b of its corresponding interlocking portion 34 of the boss portion 32, is moved to the top position 34a1 of the adjacent interlocking portion 34, as shown in FIG. 17, the two engaging arms 47a and 47b of the head body 44 are elastically deformed so that the slit 45 between them is maximally spread. Thereupon, a preset value is reached by torque that is applied to the boss portion 32 by the wrench 41.

Thereafter, each of the protuberances 46a and 46b of the torque wrench 41 moves along the slope 34b of its corresponding interlocking portion 34 of the boss portion 32 and gets beyond the top position 34a1 of the adjacent interlocking portion 34. At this point in time, the interlocking portions 34 are disengaged from the protuberances 46a and 46b, as shown in FIG. 18. Consequently, the elastically deformable portions 48 of the head body 44 are activated to prevent torque higher than a preset value from being applied to the boss portion 32.

When the protuberances 46a and 46b of the torque wrench 41 are disengaged from the interlocking portions 34 of the boss portion 32, furthermore, the engaging arms 47a and 47b of the wrench 41 are rapidly elastically restored to their original shapes, as shown in FIG. 18. As each of the engaging arms 47a and 47b in its initial state strikes the bottom position 34a2 of the slope 34b of the interlocking portion 34 adjacent to that interlocking portion 34 in mesh with the corresponding protuberance 46a or 46b, therefore, a click feeling, as well as a clock sound, is produced. Thus, the state of the torque wrench 41 rotated to its final position of the tightening direction can be reliably recognized, and the screw portion 12 of the ultrasonic probe 11 can be correctly tightened into the threaded hole portion 10a of the horn 10 of the ultrasonic vibrator 6 with preset torque.

Further, the torque wrench 41 of the present embodiment can also be used to remove the screw portion 12 of the ultrasonic probe 11 from the threaded hole portion 10a of the horn 10 of the ultrasonic vibrator 6. In this removal operation, as shown in FIG. 14, the wrench 41 is secured to the hand piece 1 of the ultrasonic treatment instrument, and its head 43 is held in releasable engagement with the boss portion 32 of the treatment instrument.

In the set state, as shown in FIG. 15, the two engaging arms 47a and 47b engage with the boss portion 32, and the interlocking portions 34 formed on the outer peripheral surface of the boss portion 32 are kept in an initial state such that one of them is in mesh with the protuberance 46a, and another is in mesh with the protuberance 46b. In this initial state, the torque wrench 41 is rotated counterclockwise that is the opposite direction to the tightening direction. During this operation, the stop surface 46a2 or 46b2 of each of the two protuberances 46a and 46b abuts the vertical wall portion 34a of its corresponding interlocking portion 34 of the boss portion 32. Therefore, the torque of the wrench 41 is transmitted directly from each of the protuberances 46a and 46b to the vertical wall portion 34a of its corresponding interlocking portion 34 of the boss portion 32 without causing the slit 45 between the engaging arms 47a and 47b of the wrench 41 to widen. Consequently, torque in the direction to remove the screw portion 12 of the ultrasonic probe 11 from the threaded hole portion 10a of the horn 10 of the ultrasonic vibrator 6 can be transmitted from the engaging arms 47a and 47b of the head body 44 to the boss portion 32. Further, the screw portion 12 of the probe 11 can be easily removed from the threaded hole portion 10a of the horn 10 of the vibrator 6.

The above structure has the following technical meanings. Specifically, according to the present embodiment, the slit 45 of the torque wrench 41 gradually opens as the wrench 41 is rotated in the tightening direction. When the tightening torque reaches a certain value, the protuberances 46a and 46b of the head body 44 are disengaged from their corresponding interlocking portions 34 of the boss portion 32 of the rotary knob 23. In this way, a tightening portion between the screw portion 12 of the ultrasonic probe 11 and the threaded hole portion 10a of the horn 10 of the ultrasonic vibrator 6 can be tightened with a predetermined torque. Thus, the elastically deformable portions 48 of the head body 44, limiting the torque, formed with the slit 45 in the head 43 can be integrated with the head 43 and arm 42. Accordingly, the arm 42, the head 43, and the elastically deformable portions 48 of the head body 44 of the torque wrench 41 can be formed as an integral part. Thus, the number of constituent parts of the torque wrench 41 can be reduced to lower cost.

Further, the wide portion 49 is disposed on the distal end side of the slit 45 of the head 43 of the torque wrench 41. Slit width L3 of the wide portion 49 is greater than the outside diameter of the outer sheath 18 of the sheath body 16 of the hand piece 1 of the ultrasonic treatment instrument. Therefore, the head 43 of the wrench 41 can be secured to the sheath body 16 of the hand piece 1 in such a manner that the sheath body 16 is laterally introduced into the wide portion 49 of the slit 45. Thus, when compared with the case of a conventional torque wrench where the sheath body 16 of the hand piece 1 is introduced from its distal end into a sleeve, the head 43 of the torque wrench 41 can be more easily secured to the sheath body 16 of the hand piece 1, so that the operability of the wrench 41 is improved.

Since the inside diameter of a trocar cannula is generally determined, a sheath portion (or the sheath body 16) to be passed through the cannula is formed with a diameter smaller than the inside diameter of the cannula. Thus, it is difficult in design to provide the sheath body 16 having a small diameter with an engagement portion used as a torque wrench receiving portion. According to the present embodiment, therefore, design difficulties can be overcome by disposing the boss portion 32 as the torque wrench receiving portion on the rotary knob 23, which is larger in diameter than the sheath body 16 and is located on the proximal end side of the sheath body.

Further, the four recesses 33 are arranged in the outer peripheral surface at the distal end of the boss portion 32 of the rotary knob 23, and the guide portions 35 in the form of sloped cuts are provided individually beside the recesses 33. When the torque wrench 41 is operated, the protuberances 46a and 46b of the head body 44 are individually guided along the guide portions 35 and engage with the interlocking portions 34 of the boss portion 32. Accordingly, the torque wrench 41 cannot be disengaged from the boss portion 32 of the knob 23 during the tightening operation. Thus, the operability of the wrench 41 is improved.

Furthermore, the torque wrench 41 can be handled in the same way using the same part (head 43) of it in both the operations to tighten the screw portion 12 of the ultrasonic probe 11 into the threaded hole portion 10a of the horn 10 of the ultrasonic vibrator 6 and to remove the screw portion 12 from the threaded hole portion 10a. Thus, a user can easily handle the torque wrench 41 with improved convenience.

FIGS. 19 to 24 show a second embodiment of the present invention. According to the first embodiment (FIGS. 1 to 18), the engagement portion used as the torque wrench receiving portion is attached to the boss portion 32 of the rotary knob 23. According to the second embodiment, in contrast, a large-diameter boss portion (engagement portion) 51 as a torque wrench receiving portion is integrally provided on an ultrasonic probe 11 of an ultrasonic treatment instrument. The boss portion 51 is constructed in the same manner as the boss portion 32 of the rotary knob 23 of the first embodiment. Portions other than the boss portion 51 are constructed in the same manner as their counterparts in the first embodiment, so that like numbers are used to designate the like portions, and a repeated description thereof is omitted herein.

Figure 19:
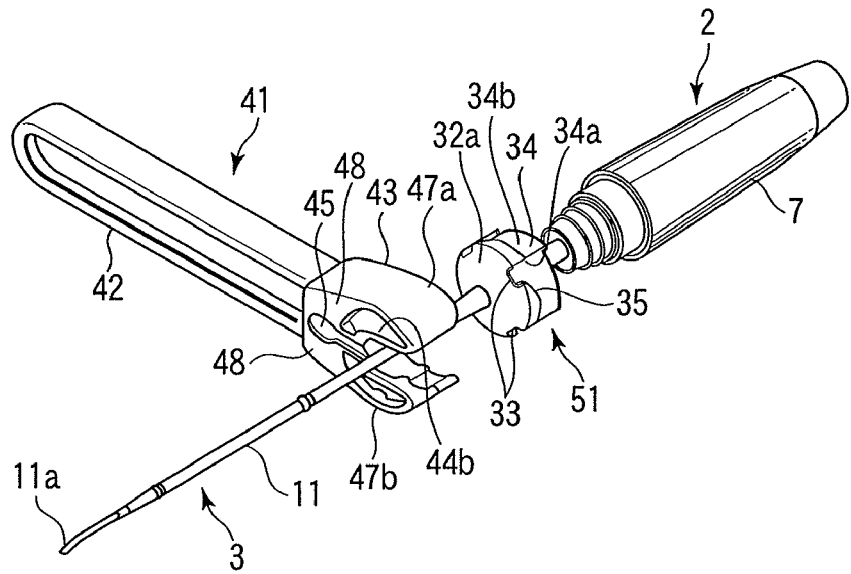
FIG. 19 is a perspective view showing how a torque wrench according to a second embodiment of the invention is operated to attach or detach a threaded engagement portion between an ultrasonic vibrator and an ultrasonic probe.
Figure 20:
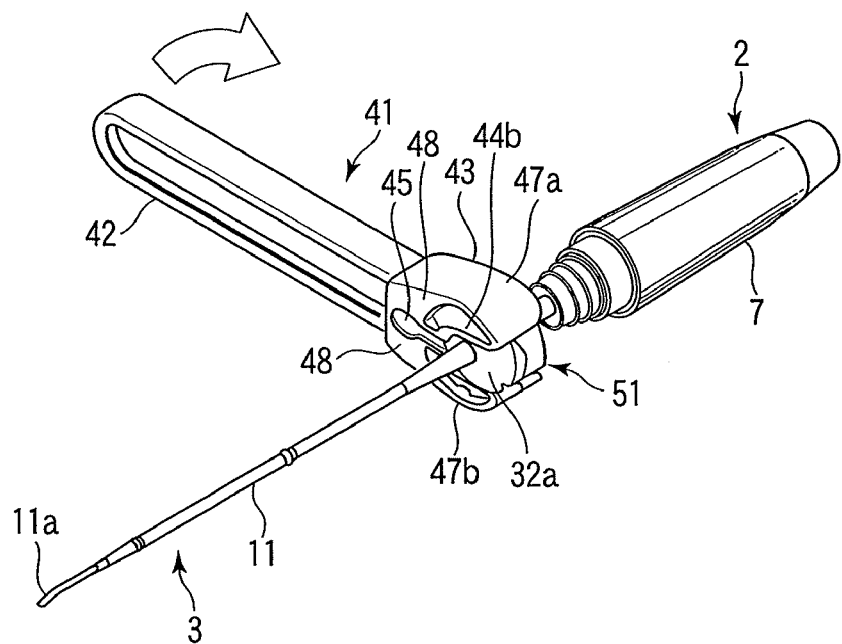
FIG. 20 is a view explaining how the torque wrench according to the second embodiment is operated.
Figure 21:
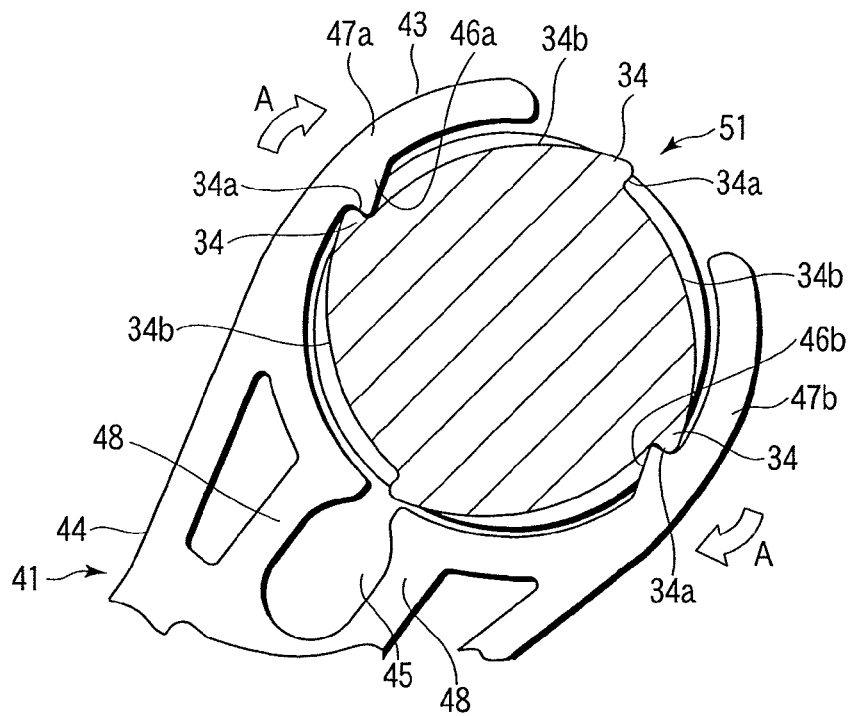
FIG. 21 is a plan view showing an initial state before the operative torque wrench according to the second embodiment is rotated in its tightening direction.

In the present embodiment, a torque wrench 41 similar to that of the first embodiment is used to tighten a screw portion 12 of the ultrasonic probe 11 into a threaded hole portion 10a of a horn 10 of an ultrasonic vibrator 6. In operating the torque wrench 41 of the present embodiment, as shown in FIG. 19, the probe 11 is passed through a wide portion 49 of a slit 45 of the wrench 41. In this state, a head 43 of the wrench 41 is slid to the proximal end portion of the probe 11 and caused to releasably engage with the boss portion 51 of the probe 11, as shown in FIG. 20. When this is done, a protuberance 46a of a head body 44 is introduced from one of recesses 33 provided in the outer peripheral surface of the boss portion 51 into a region on the outer peripheral surface side of the boss portion. Likewise, a protuberance 46b is introduced from another recess 33 into a region on the outer peripheral surface side of the boss portion 51. Further, the protuberances 46a and 46b are guided individually through their corresponding guide portions 35 of the boss portion 51 to their corresponding interlocking portions 34. Thus, the head 43 of the torque wrench 41 is set in such a state that it is in releasable engagement with the boss portion 51 of the probe 11. In the set state, as shown in FIG. 21, two engaging arms 47a and 47b engage with the boss portion 51, and the protuberances 46a and 46b are kept individually in mesh with the interlocking portions 34 formed on the outer peripheral surface of the boss portion 51. As this is done, the torque wrench 41 is held in its initial state before it is rotated in its tightening direction.

Thereafter, the torque wrench 41 is rotated clockwise, as indicated by arrow A in FIG. 21. By this operation, the torques are individually transmitted from the protuberances 46a and 46b of the torque wrench 41 to the interlocking portions 34 of the boss portion 51. When this is done, the ultrasonic probe 11 is rotated around its axis by tightening force that acts on the boss portion 51 of the ultrasonic probe 11. Thereupon, tightening torque is transmitted that causes the screw portion 12 of the probe 11 to rotate so as to be tightened into the threaded hole portion 10a of the horn 10 of the ultrasonic vibrator 6.

Figure 22:
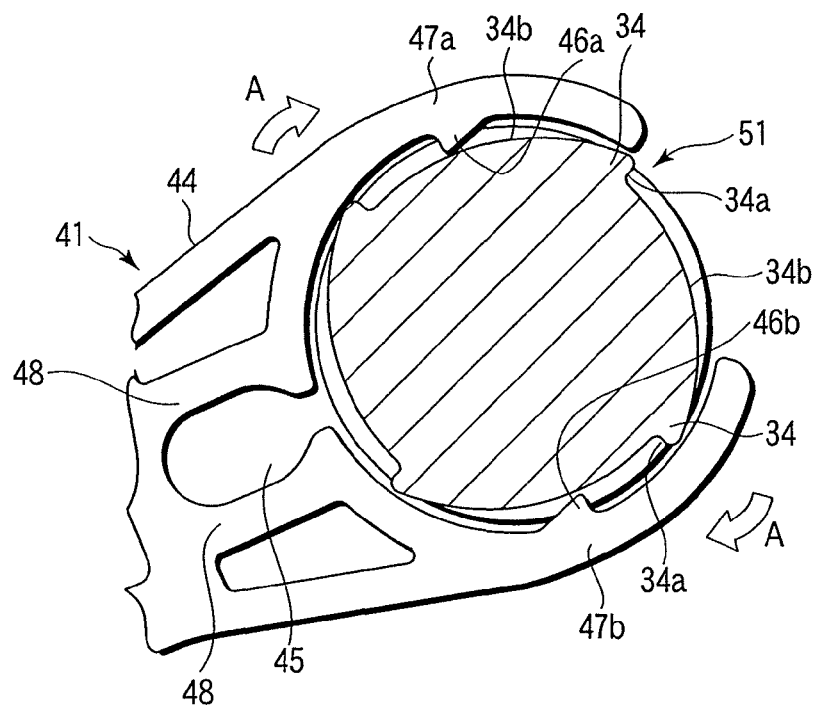
FIG. 22 is a plan view showing the operative torque wrench according to the second embodiment being rotated in the tightening direction.

When the torque wrench 41 is rotated clockwise, moreover, each of its protuberances 46a and 46b moves from a bottom position 34a2 of a vertical wall portion 34a of its corresponding interlocking portion 34 of the boss portion 51 toward a top position 34a1 of an adjacent vertical wall portion 34a in such a manner that it slides on a slope 34b of the interlocking portion 34, as shown in FIG. 22. Thus, as the protuberances 46a and 46b slide individually on the respective slopes 34b of their corresponding interlocking portions 34, the slit 45 between the two engaging arms 47a and 47b of the head body 44 is gradually widened, so that the head body 44 is elastically deformed.

Figure 23:
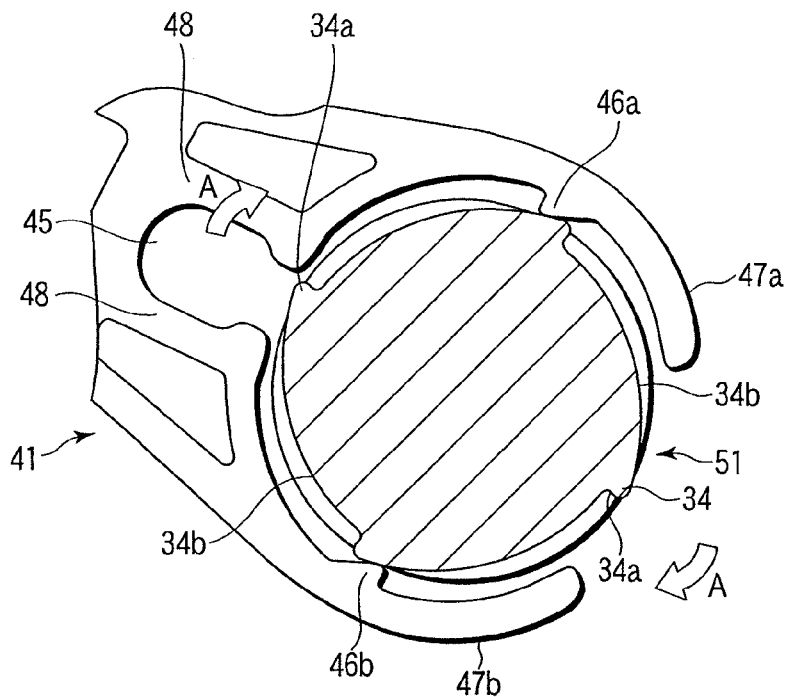
FIG. 23 is a plan view showing a state just before the operative torque wrench according to the second embodiment is rotated to its final rotational position of the tightening direction.

When each of the protuberances 46a and 46b of the torque wrench 41, sliding on the slope 34b of its corresponding interlocking portion 34 of the boss portion 51, is moved to the top position 34a1 of the adjacent interlocking portion 34, as shown in FIG. 23, the two engaging arms 47a and 47b of the head body 44 are elastically deformed so that the slit 45 between them is maximally spread. Thereupon, a preset value is reached by torque that is applied to the boss portion 51 by the torque wrench 41.

Figure 24:
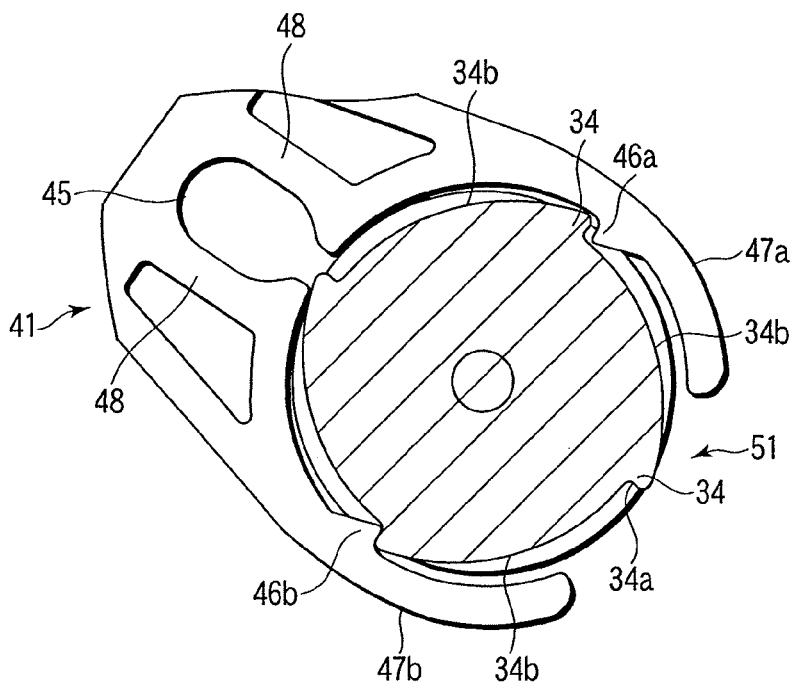
FIG. 24 is a plan view showing a state in which the operative torque wrench according to the second embodiment is in the final rotational position of the tightening direction.

Thereafter, each of the protuberances 46a and 46b of the torque wrench 41 slides along the slope 34b of its corresponding interlocking portion 34 of the boss portion 51 and gets beyond the top position 34a1 of the adjacent interlocking portion 34. At this point in time, the interlocking portions 34 are disengaged from the protuberances 46a and 46b, as shown in FIG. 24. Consequently, the elastically deformable portions 48 of the head body 44 are activated to prevent torque higher than a preset value from being applied to the boss portion 51.

When the protuberances 46a and 46b of the torque wrench 41 are disengaged from the interlocking portions 34 of the boss portion 51, furthermore, the engaging arms 47a and 47b of the wrench 41 are rapidly elastically restored to their original shapes, as shown in FIG. 24. As each of the engaging arms 47a and 47b in its initial state strikes the bottom position 34a2 of the slope 34b of the interlocking portion 34 adjacent to that interlocking portion 34 in mesh with the corresponding protuberance 46a or 46b, therefore, a click feeling, as well as a clock sound, is produced. Thus, the state of the torque wrench 41 rotated to its final position of the tightening direction can be reliably recognized, and the screw portion 12 of the ultrasonic probe 11 can be correctly tightened into the threaded hole portion 10a of the horn 10 of the ultrasonic vibrator 6 with preset torque.

Also in the present embodiment, the torque wrench 41 can be used to remove the screw portion 12 of the ultrasonic probe 11 from the threaded hole portion 10a of the horn 10 of the ultrasonic vibrator 6. In this removal operation, as shown in FIG. 20, the head 43 of the wrench 41 is held in releasable engagement with the boss portion 51 of the probe 11.

In the set state, as shown in FIG. 21, the two engaging arms 47a and 47b engage with the boss portion 51, and the interlocking portions 34 formed on the outer peripheral surface of the boss portion 51 are kept in an initial state such that one of them is in mesh with the protuberance 46a, and another is in mesh with the protuberance 46b. In this initial state, the torque wrench 41 is rotated counterclockwise that is the opposite direction to the tightening direction of the wrench 41. During this operation, the stop surface 46a2 or 46b2 of each of the two protuberances 46a and 46b abuts the vertical wall portion 34a of its corresponding interlocking portion 34 of the boss portion 51. Therefore, the torque of the wrench 41 is transmitted directly from each of the protuberances 46a and 46b to the vertical wall portion 34a of its corresponding interlocking portion 34 of the boss portion 51 without causing the slit 45 between the engaging arms 47a and 47b of the wrench 41 to widen. Consequently, torque in the direction to remove the screw portion 12 of the ultrasonic probe 11 from the threaded hole portion 10a of the horn 10 of the ultrasonic vibrator 6 can be transmitted from the engaging arms 47a and 47b of the head body 44 to the boss portion 51. Further, the screw portion 12 of the probe 11 can be easily removed from the threaded hole portion 10a of the horn 10 of the vibrator 6.

The above structure has the following technical meanings. Specifically, according to the present embodiment, the large-diameter boss portion (engagement portion) 51 as the torque wrench receiving portion is integrally provided on the ultrasonic probe 11 of an ultrasonic treatment instrument. Thus, by securing the head 43 of the torque wrench 41 to the boss portion 51, the wrench 41 can be used in the same manner as in the first embodiment during the operation to tighten the screw portion 12 of the probe 11 into the threaded hole portion 10a of the horn 10 of the ultrasonic vibrator 6.

Figure 25:
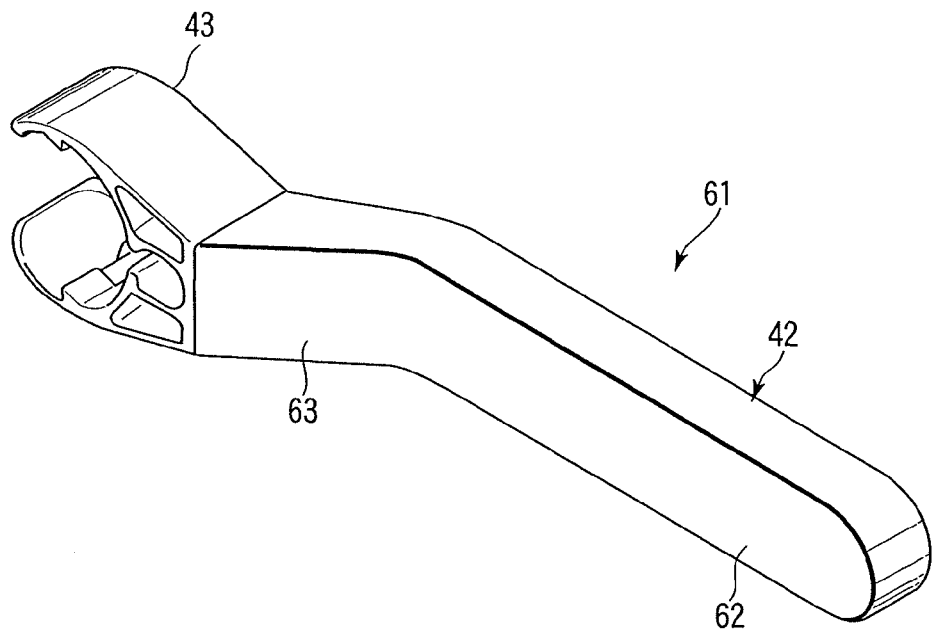
FIG. 25 is a perspective view showing a torque wrench according to a modification of the first embodiment.
Figure 26:
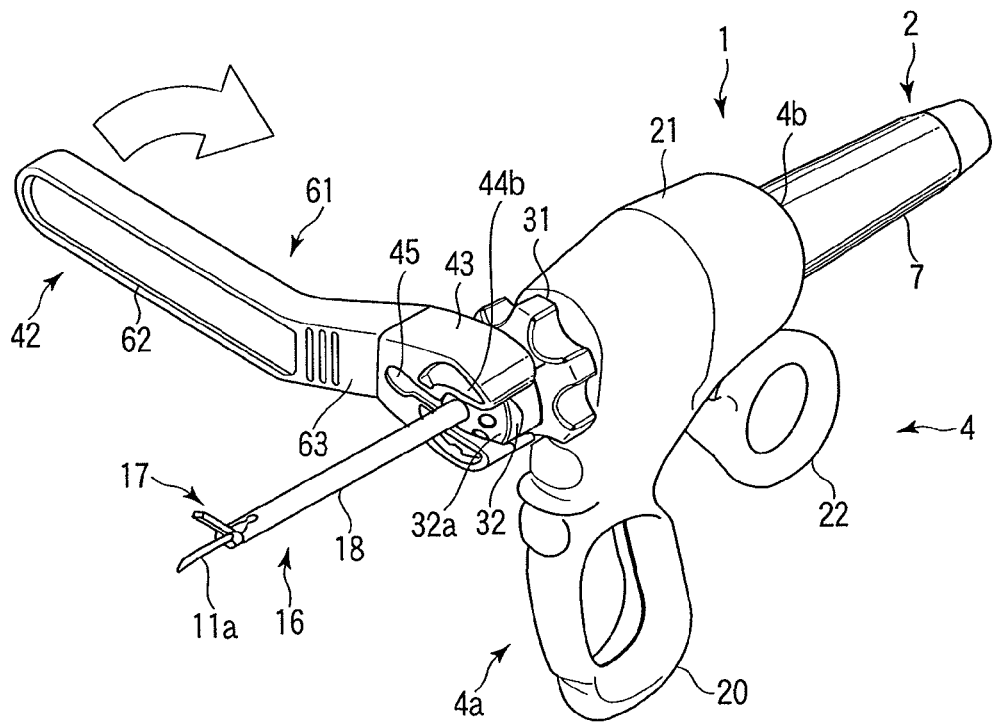
FIG. 26 is a perspective view showing how the torque wrench according to the modification of the first embodiment is secured.

FIGS. 25 and 26 show a modification of the torque wrench 41 of the first embodiment (FIGS. 1 to 18). The arm 42 of the torque wrench 41 of the first embodiment is straight as a whole. In contrast, an arm 42 of a torque wrench 61 of this modification includes a straight grip portion 62, and a bent portion 63 which is located at a junction with a head 43 and bent from the grip portion 62. As shown in FIG. 26, the bent portion 63 of the arm 42 is bent so that the grip portion 62 is away from the control section 4a of the handle unit 4 of the ultrasonic treatment instrument when the head 43 is caused to releasably engage with the boss portion 32 of the rotary knob 23 during use of the wrench 61.

According to this modification, therefore, the hand of the operator holding the grip portion 62 of the arm 42 of the torque wrench 61 can be prevented from interfering with the control section 4a of the handle unit 4. Specifically, in holding the arm 42 of the wrench 61, the hand may interfere with the control section 4a of the handle unit 4, depending on the positional relationship between the wrench 61 and the control section 4a of the handle unit 4. Thus, if the bent portion 63 of the wrench 61 is bent so that the grip portion 62 is away from the control section 4a of the handle unit 4, as in this modification, in holding the arm 42 of the wrench 61, the hand can be prevented from interfering with the control section 4a of the handle unit 4.

The following are appendixes containing other technical features of the present invention.

Note:

(Appendix 1) A torque wrench used in attachment and detachment of an ultrasonic vibrator and an ultrasonic probe threadedly engaged with each other in an ultrasonic treatment instrument, comprising:

an arm which is held by a user;

a head which is integrally provided on a distal end portion of the arm and which is configured to engage with an engagement portion provided on the ultrasonic probe or a sheath which covers the ultrasonic probe;

at least one protuberance provided on an engaging surface of an engaging portion of the head;

a slit provided on the distal end side of the head; and a torque limiting mechanism in which a disengagement between the protuberance and a projection provided on an outer peripheral surface of the engagement portion because of the widened slit is prevented when torque higher than a preset value is applied to the engagement portion with the protuberance in mesh with the projection of the engagement portion, thereby the torque higher than the preset value being prevented from being applied to the engagement portion.

(Appendix 2) The torque wrench according to Appendix 1, wherein the slit includes a wide portion which has a width substantially equal to or greater than the outside diameter of the ultrasonic probe/the sheath.

(Appendix 3) The torque wrench according to Appendix 1, wherein the engagement portion is provided on a knob portion configured to rotate the sheath.

(Appendix 4) A torque wrench used in attachment and detachment of an ultrasonic vibrator and an ultrasonic probe threadedly engaged with each other in an ultrasonic treatment instrument, comprising:

an arm which is held by a user; and a head which is integrally provided on a distal end portion of the arm and which is configured to releasably engage with an engagement portion disposed on a proximal end portion of an insertion section of the ultrasonic treatment instrument to be inserted into a human body and to transmit torque to the ultrasonic probe, wherein the head includes a head body including an engaging portion capable of engaging with the engagement portion, and a slit formed by cutting a part of a peripheral wall surface, and the head body covering an outer peripheral surface of the engagement portion with the engaging portion in engagement with the engagement portion, at least one protuberance which protrudes inward from an inner peripheral surface of the head body, each protuberance/protuberances including a slope the height of projection, from the head body, of which gradually increases along the circumference of the head body and which is oriented in a direction of rotation during a rotating operation such that the ultrasonic probe is tightened into the ultrasonic vibrator, and a stop surface extending in radial directions of the head body, and an elastically deformable portion configured to cause at least one of two opposite side portions of the slit of the head body to be elastically deformed so that the slit is widened until a preset value is reached by torque applied from the engaging portion to the engagement portion with the protuberance in mesh with an interlocking portion formed on the outer peripheral surface of the engagement portion.

(Appendix 5) An ultrasonic surgical device comprising:

an ultrasonic treatment instrument including an ultrasonic vibrator configured to generate ultrasonic vibration, an ultrasonic probe a proximal end of which is threadedly engaged with the ultrasonic vibrator and which is capable of transmitting the ultrasonic vibration produced by the ultrasonic vibrator from the proximal end to a distal end, and an engagement portion provided at a proximal end portion of an insertion section to be inserted into a human body; and a torque wrench used in attachment and detachment of the ultrasonic vibrator and the ultrasonic probe, the torque wrench including an arm which is held by a user, and a head which is provided on a distal end portion of the arm so as to be integral with the arm and which is configured to releasably engage with the engagement portion of the ultrasonic treatment instrument and to transmit torque to the ultrasonic probe, wherein the head includes a head body including an engaging portion capable of engaging with the engagement portion, and a slit formed by cutting a part of a peripheral wall surface, the head body covering an outer peripheral surface of the engagement portion with the engaging portion in engagement with the engagement portion, at least one protuberance which protrudes inward from an inner peripheral surface of the head body, each protuberance/protuberances including a slope the height of projection, from the head body, of which gradually increases along the circumference of the head body and which is oriented in a direction of rotation during a rotating operation such that the ultrasonic probe is tightened into the ultrasonic vibrator, and a stop surface extending in radial directions of the head body, and an elastically deformable portion configured to cause at least one of two opposite side portions of the slit of the head body to be elastically deformed so that the slit is widened until a preset value is reached by torque applied from the engaging portion to the engagement portion with the protuberance in mesh with an interlocking portion formed on the outer peripheral surface of the engagement portion.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A torque wrench used in attachment and detachment of an ultrasonic vibrator and an ultrasonic probe of an ultrasonic treatment instrument, comprising:

an arm portion which is held by a user; and a head portion which is provided on a distal end portion of the arm portion so as to be integral with the arm portion, and which is configured to releasably engage with an engagement portion disposed on the ultrasonic treatment instrument and to transmit torque to the engagement portion, wherein the head portion includes an engaging portion covering an outer peripheral surface of the engagement portion and capable of engaging with the engagement portion, a slit formed by cutting a part of a peripheral wall surface of the engaging portion, a protuberance which protrudes inward from the peripheral wall surface of the engaging portion, and which meshes with an interlocking portion formed on the outer peripheral surface of the engagement portion and having a top position and a bottom position, the protuberance moving the interlocking portion from the bottom position toward the top position when the torque is transmitted to the engagement portion in a rotating operation such that the ultrasonic probe and the ultrasonic vibrator are threadedly engaged with each other, and the protuberance including a slope the height of projection, from the peripheral wall surface, of which gradually increases along the circumference of the peripheral wall and which is oriented in a direction of rotation when the torque is transmitted to the engagement portion in the rotating operation such that the ultrasonic probe and the ultrasonic vibrator are threadedly engaged with each other, and a stop surface extending in radial directions of the engaging portion, and an elastically deformable portion configured to cause at least one of two opposite side portions of the slit to be elastically deformed so that the slit is widened until the protuberance reaches the top position of the interlocking portion such that a preset value is reached by the torque applied from the engaging portion, and configured to cause the at least one of the two opposite side portions of the slit to be elastically restored when the protuberance gets beyond the top position of the interlocking portion such that torque higher than the preset value is prevented from being applied to the engagement portion to the engagement portion with the protuberance in mesh with an interlocking portion formed on the outer peripheral surface of the engagement portion.

2. The torque wrench according to claim 1, wherein the slit includes a wide portion which is wide enough to allow passage of an insertion section of the ultrasonic treatment instrument to be inserted into a body cavity and which is wider than other parts of the slit.

3. The torque wrench according to claim 1, wherein the protuberance of the head portion is guided to move opposite to the direction in which the head portion is disengaged by a guide portion on the engagement portion of the ultrasonic treatment instrument during the rotating operation, thereby the protuberance being prevented from being disengaged from the engagement portion of the head portion.

4. The torque wrench according to claim 1, wherein the head portion includes an abutting surface configured to abut an instrument-side abutting surface on the engagement portion of the ultrasonic treatment instrument during the rotating operation.

5. The torque wrench according to claim 4, wherein the abutting surface of the head portion is shaped corresponding to the instrument-side abutting surface of the engagement portion.

6. The torque wrench according to claim 1, wherein the protuberance of the head portion is guided to move opposite to the direction in which the head portion is disengaged by a guide portion in the form of a slope on the engagement portion of the ultrasonic treatment instrument during the rotating operation, the head portion includes an abutting surface configured to abut an instrument-side abutting surface on the engagement portion of the ultrasonic treatment instrument during the rotating operation, and the abutting surface of the head portion is shaped corresponding to the instrument-side abutting surface of the engagement portion, thereby a backlash during the rotating operation being prevented.

* * * * *